(12) United States Patent
Takahashi et al.

(10) Patent No.: US 8,372,583 B2
(45) Date of Patent: Feb. 12, 2013

(54) POTENTIATOR OF ACTIVITY OF ANTI-CANCER AGENT AND USE THEREOF, AND BIOMARKER FOR PREDICTION OF PROGNOSIS IN CANCER PATIENT AND USE THEREOF

(75) Inventors: Masahide Takahashi, Nagoya (JP); Takuya Kato, Nagoya (JP); Fumitaka Kikkawa, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 0 days.

(21) Appl. No.: 13/060,314

(22) PCT Filed: Aug. 27, 2009

(86) PCT No.: PCT/JP2009/004162
§ 371 (c)(1),
(2), (4) Date: Feb. 23, 2011

(87) PCT Pub. No.: WO2010/023917
PCT Pub. Date: Mar. 4, 2010

(65) Prior Publication Data
US 2011/0160287 A1   Jun. 30, 2011

(30) Foreign Application Priority Data
Sep. 1, 2008 (JP) ................................. 2008-223461

(51) Int. Cl.
*C12Q 1/68* (2006.01)
*C07H 21/04* (2006.01)
*C07H 21/02* (2006.01)

(52) U.S. Cl. ....... 435/6; 536/23.1; 536/24.3; 536/24.31; 536/24.33

(58) Field of Classification Search ........................ None
See application file for complete search history.

(56) References Cited

U.S. PATENT DOCUMENTS
2003/0203363 A1* 10/2003 Spytek et al. ..................... 435/6
2004/0146921 A1   7/2004 Eveleigh et al.

FOREIGN PATENT DOCUMENTS
WO   WO-2005005601 A2   1/2005

OTHER PUBLICATIONS

Yang, X.-J. et al., "The Rpd3/Hda1 family of lysine deacetylases: from bacteria and yeast to mice and men," Nat Rev Mol Cell Biol., vol. 9, 2008, pp. 206-218.
Bolden, J. E. et al., "Anticancer activities of histone deacetylase inhibitors," Nat Rev Drug Discov., vol. 5, 2006, pp. 769-784.
Minucci, S. et al., "Histone deacetylase inhibitors and the promise of epigenetic (and more) treatments for cancer," Nature Reviews Cancer, vol. 6, 2006, pp. 38-51.
Xu, W. S. et al., "Histone deacetylase inhibitors: molecular mechanisms of action," Oncogene. 26, 2007, pp. 5541-5552.
Marks, P. A. et al., "Dimethyl sulfoxide to vorinostat: development of this histone deacetylase inhibitor as an anticancer drug," Nature Biotechnology, vol. 25, No. 1, 2007, pp. 84-90.
Miyajima, A. et al. "Role of reactive oxygen species in cis-dichlorodiammineplatinum-induced cytotoxicity on bladder cancer cells," Br J Cancer. 76(2), 1997, pp. 206-210.
Kurosu, T. et al., "BCL6 overexpression prevents increase in reactive oxygen species and inhibits apoptosis induced by chemotherapeutic reagents in B-cell lymphoma cells," Oncogene. 22, 2003, pp. 4459-4468.
Hwang, IT. et al., "Drug resistance to 5-FU linked to reactive oxygen species modulator 1," Biochem Biophys Res Commun. 359, 2007, pp. 304-310.
Ravid, A. et al. "1,25-Dihydroxyvitamin $D_3$ enhances the susceptibility of breast cancer cells to doxorubicin-induced oxidative damage," Cancer Res. 59, 1999, pp. 862-867.
Godwin, A. K. et al. "High resistance to cisplatin in human ovarian cancer cell lines is associated with marked increase of glutathione synthesis," Proc Natl Acad Sci U S A. vol. 89, 1992, pp. 3070-3074.
Yokomizo, A. et al. "Cellular levels of thioredoxin associated with drug sensitivity to cisplatin, mitomycin C, doxorubicin and etoposide," Cancer Res. 55, 1995, pp. 4293-4296.
Sasada, T. et al., "Redox control of resistance to cis-diamminedichloroplatinum (II) (CDDP), protective effect of human thioredoxin against CDDP-induced cytotoxicity," J Clin Invest., vol. 97, No. 10, 1996, pp. 2268-2276.
Powis, G. et al., "Thioredoxin signaling as a target for cancer therapy," Curr Opin Pharmacol. 7, 2007, pp. 392-397.
Halkidou, K. et al., "Upregulation and nuclear recruitment of HDAC1 in hormone refractory prostate cancer," Prostate 59, 2004, pp. 177-189.
Glozak, MA et al., "Histone deacetylases and cancer," Oncogene 26, 2007, pp. 5420-5432.
Takahashi, M et al., "Developmentally regulated expression of a human "finger"-containing gene encoded by the 5' half of the ret transforming gene," Mol Cell Biol., vol. 8, No. 4, 1988, pp. 1853-1856.
Tezel, G. et al. "Different nuclear/cytoplasmic distributions of RET finger protein in different cell types," Pathol. Int. 49, 1999, pp. 881-886.

(Continued)

*Primary Examiner* — Amy Bowman
(74) *Attorney, Agent, or Firm* — Edwards Wildman Palmer LLP; James E. Armstrong, IV; Andy Shyjan

(57) ABSTRACT

Disclosed is a means for improving the clinical outcomes of cancer therapy. Specifically disclosed is an activity potentiator comprising a compound capable of inhibiting the expression of RFP (RET finger protein) gene or the activity of RFP as an active ingredient. The activity of an anti-cancer agent having an oxidative stress inducing ability can be potentiated by using the anti-cancer agent in combination with the activity potentiator. Further specifically disclosed are a biomarker useful for the recognition of prognosis in a cancer patient and use of the biomarker.

4 Claims, 11 Drawing Sheets

OTHER PUBLICATIONS

Takahashi, M. et al., "*ret* transforming gene encodes a fusion protein homologous to tyrosine kinases," Mol. Cell. Biol., vol. 7, No. 4, 1987, pp. 1378-1385.

Shimono, Y. et al., "RET finger protein is a transcriptional repressor and interacts with enhancer of polycomb that has dual transcriptional functions," J. Biol Chem., vol. 275, No. 50, 2000, pp. 39411-39419.

Shimono, Y. et al., "Mi-2β associates with BRG1 and RET finger protein at the distinct regions with transcriptional activating and repressing abilities," J. Biol. Chem., vol. 278, No. 51, 2003, pp. 51638-51645.

Shimono, K. et al., "Microspherule protein 1, Mi-2β, and RET finger protein associate in the nucleolus and up-regulate ribosomal gene transcription," J. Biol. Chem., vol. 280, No. 47, 2005, pp. 39436-39447.

Lee, E. L. et al., "Impaired Activity of Volume-Sensitive Cl⁻ Channel Is Involved in Cisplatin Resistance of Cancer Cells," Journal of Cellular Physiology, 211, 2007, pp. 513-521.

Luo, D. et al, "TSA increasing the sensitivity of human ovarian cancer cell line C13 to cisplatin in vitro," Zhongliu, 26(10), 2006, p. 882-886, CAPLUS [online], [retrieved on Sep. 16, 2009] Accession No. 2008:80273 (1 page).

Bloor, A. JC, et al, "RFP represses transcriptional activation by bHLH transcription factors," Oncogene, 24, 2005, pp. 6729-6736.

Fukushige, S. et al, "RET finger protein enhances MBD2-and MBD4-dependent transcriptional repression," Biochemical and Biophysical Research Communications, 351, 2006, pp. 85-92.

Townson, S. M. et al, "Novel role of the RET finger protein in estrogen receptor-mediated transcription in MCF-7 cells," Biochemical and Biophysical Research Communications, 349, 2006, pp. 540-548.

Krutzfeldt, M. et al, "Selective Ablation of Retinoblastoma Protein Function by the RET Finger Protein," Molecular Cell, vol. 18, 2005, pp. 213-224.

Dho, S. H. et al., "The Ret Finger Protein Induces Apoptosis via Its RING Finger-B Box-Coiled-coil Motif," The Journal of Biological Chemistry, vol. 278, No. 34, 2003, pp. 31902-31908.

Kato, T. et al, "Characterization of the HDAC1 Complex That Regulates the Sensitivity of Cancer Cells to Oxidative Stress," Cancer Research, 69(8), 2009, pp. 3597-3604.

Tsukamoto, H. et al, "Expression of Ret Finger Protein correlates with outcomes in endometrial cancer," Cancer Science, vol. 100, No. 10, 2009, pp. 1895-1901, Online publication Jul. 10, 2009.

International Search Report dated Oct. 6, 2009, issued for PCT/JP2009/004162.

Zachariah E. Selvanayagam et al., "Prediction of chemotherapeutic response in ovarian cancer with DNA microarray expression profiling," Cancer Genetics and Cytogenetics, vol. 154, Oct. 2004, pp. 63-66.

Gaye Tezel et al., "Differential expression of RET finger protein in testicular germ cell tumors," Pathology International, vol. 52, Oct. 2002, pp. 623-627.

Jin Xiang-Qun et al., "Expression Levels of RFP in Normal and Cancer Human Tissues *via* Real-time RT-PCR Detection," Chemical Research in Chinese Universities, vol. 22, No. 4, Jul. 2006, pp. 443-446.

Takuya Kato et al., "Characterization of the HDAC1 Complex That Regulates the Sensitivity of Cancer Cells to Oxidative Stress," Cancer Research, vol. 69, No. 8, Jan. 2009, pp. 3597-3604 and a cover page.

Hirohisa Tsukamoto et al., "Expression of Ret finger protein correlates with outcomes in endometrial cancer", Cancer Science, vol. 100, No. 10, Oct. 2009, pp. 1895-1901.

Supplementary European Search Report dated Jan. 27, 2012, issued for the corresponding European patent application No. 09809573.0.

\* cited by examiner

SEQUENCE LISTING

<160> NUMBER OF SEQ ID NOS: 18

<210> SEQ ID NO 1
<211> LENGTH: 2969
<212> TYPE: DNA
<213> ORGANISM: Homo sapiens

<400> SEQUENCE: 1

```
gggtttacgc tgccgccggc atccgctcgg acgcggccac gttgtcttgc gcgctttgcc      60
cgcctggccc tgggactctg accctcggct acccttcct gccccactag cgtggccgcg     120
agcctcggtg agccggccgt attccgctc tcgcttaggg ggcacaggcg caggcatcgg     180
cccggccact ccaagccttc ggtgcgcggg cgcgtctggg atacgggccc gggaggcgcc     240
gccctccgtc cgcccggtgc ctctcaggaa cagcgaaccg agagagcgc cggagagttg     300
ggctcagtgc agagctcggc gccggggccc atgcccgtgc cccccgcag gccggcgcca     360
tggcctccgg gagtgtggcc gagtgcctgc agcaggagac cacctgcccc gtgtgcctgc     420
agtacttcgc agagcccatg atgctcgact gcggccataa catctgttgc gcgtgcctcg     480
cccgctgctg gggcacggca gagactaacg tgtcgtgccc gcagtgccgg agaccttcc     540
cgcagaggca catgcggccc aaccggcacc tggccaacgt gacccaactg gtaaagcagc     600
tgcgcaccga gcggccgtcg gggcccggcg gcgagatggg cgtgtgcgag aagcaccgcg     660
agccctgaa gctgtactgc gaggaggacc agatgcccat ctgcgtggtg tgcgaccgct     720
cccgcgagca ccgcggccac agcgtgctgc cgctcgagga ggcggtggag ggcttcaagg     780
agcaaatcca gaaccagctc gaccatttaa aaagagtgaa agatttaaag aagagacgtc     840
gggcccaggg ggaacaggca cgagctgaac tcttgagcct aacccagatg gagagggaga     900
agattgtttg ggagtttgag cagctgtatc actccttaaa ggagcatgag tatcgcctcc     960
tggcccgcct tgaggagcta gacttggcca tctacaatag catcaatggt gccatcaccc    1020
agttctcttg caacatctcc cacctcagca gcctgatcgc tcagctagaa gagaagcagc    1080
agcagcccac caggggagctc ctgcaggaca ttggggacac attgagcagg gctgaaagaa    1140
tcaggattcc tgaaccttgg atcacacctc cagatttgca agagaaaatc cacatttttg    1200
cccaaaaatg tctattcttg acggagagtc taaagcagtt cacagaaaaa atgcagtcag    1260
atatggagaa aatccaagaa ttaagagagg ctcagttata ctcagtggac gtgactctgg    1320
acccagacac ggcctacccc agcctgatcc tctctgataa tctgcggcaa gtgcggtaca    1380
gttacctcca acaggacctg cctgacaacc ccgagaggtt caatctgttt ccctgtgtct    1440
tgggctctcc atgcttcatc gccgggagac attattggga ggtagaggtg ggagataaag    1500
ccaagtggac cataggtgtc tgtgaagact cagtgtgcag aaaaggtgga gtaacctcag    1560
cccccagaa tggattctgg gcagtgtctt tgtggtatgg gaaagaatat tgggctctta    1620
cctccccaat gactgcccta cccctgcgga ccccgctcca gcgggtgggg attttcttgg    1680
actatgatgc tggtgaggtc tccttctaca acgtgacaga gaggtgtcac accttcactt    1740
tctctcatgc taccttttgt gggcctgtcc ggccctactt cagtctgagt tactcgggag    1800
ggaaaagtgc agctcctctg atcatctgcc ccatgagtgg atagatgggt ttttctggcc    1860
atgttgggaa tcatggtcat tccatggaga cctccccttg aggaggtgaa ttcaggccaa    1920
aagggctgtt ggctgtaatc ctacgccagg cacaaggcat cttgttgcct tgccacgtcc    1980
tgtcacagct gggtatcctt accatgttcc acgcccttgc agtgggagac aggatgtcca    2040
```

```
tgttctctac catccttttc cttcccatgc agattgtgaa atgtaatgag atgtatcaag      2100
atatcctaga aataaaaacc agatgtccac ctccagtgtt tcatactttc tggttttaca      2160
catcgctgga gggataaaga gtatggataa tctttggatt tggagagccg ttcaagatac      2220
ttccagcttc ttggctcagc ctggcttcct ctggttcagc cccacataat gattatggct      2280
atttgctgtc atttctgggc tagggctcct ttctaacaac ctagactgga ataaggccct      2340
gtcagcatgg ctccctttat cccagttttc cgtctgggaa cagtacctct gcccctgatt      2400
cccaatgtgc catagtttta ttaactccat taaagaagcc tgtatgtgtt ttggttagtt      2460
acagttattt tacaataatg gtgggtaatg gccccacctc tgttatgaga taatgttcta      2520
atcaatgtct ctgcctttgt atcttttctg agggctttgt ctgttctctt cattctaatg      2580
aaaggtgtat tctagtgctg ggtgcatatc atccaggata atattctgcc caactccatc      2640
ctctgttact agatccctta ccagtcacat tgtggactg gtggccagtc gtataccatc       2700
cctggaagga ttctgggaca atattccagg gattcattga cttcttggct ccttttctcc      2760
atttcctttg ggggaagggg gaattgacca tgcttaagtg catcctatca aggggcagct      2820
ccgtccccat ggccattgga tcatgagaca ctctgaagtc agaaggctgg ggcagatcac      2880
ttcaagcaag cccccatgat ggttctcagt cctgcttctc tgtgggtacg tgcccctctg      2940
tttaaaaata aactgaatat ggatgttta                                        2969

<210> SEQ ID NO 2
<211> LENGTH: 1542
<212> TYPE: DNA
<213> ORGANISM: Homo sapiens

<400> SEQUENCE: 2
atggcctccg ggagtgtggc cgagtgcctg cagcaggaga ccacctgccc cgtgtgcctg        60
cagtacttcg cagagcccat gatgctcgac tgcggccata acatctgttg cgcgtgcctc       120
gcccgctgct ggggcacggc agagactaac gtgtcgtgcc cgcagtgccg ggagaccttc       180
ccgcagaggc acatgcggcc caaccggcac ctggccaacg tgacccaact ggtaaagcag       240
ctgcgcaccg agcggccgtc ggggcccggc ggcgagatgg cgtgtgcga gaagcaccgc        300 gagcccctga gctgtactg cgaggaggac cagatgccca tctgcgtggt gtgcgaccgc        360
tcccgcgagc accgcggcca cagcgtgctg ccgctcgagg aggcggtgga gggcttcaag       420
gagcaaatcc agaaccagct cgaccattta aaaagagtga agatttaaa gaagagacgt        480 cgggcccagg ggaacaggc acgagctgaa ctcttgagcc taaccccagat ggagagggag       540 aagattgttt gggagtttga gcagctgtat cactccttaa aggagcatga gtatcgcctc       600
ctggcccgcc ttgaggagct agacttggcc atctacaata gcatcaatgg tgccatcacc       660
cagttctctt gcaacatctc ccacctcagc agcctgatcg ctcagctaga agagaagcag       720
cagcagccca ccagggagct cctgcaggac attgggggaca cattgagcag gctgaaagaa       780
atcaggattc ctgaaccttg atcacacct ccagatttgc aagagaaat ccacatttt         840 gcccaaaaat gtctattctt gacggagagt ctaaagcagt tcacagaaaa atgcagtca       900 gatatggaga aatccaagaa attaagagag gctcagttat actcagtgga cgtgactctg       960
gacccagaca cggcctaccc cagcctgatc ctctctgata tctgcggca agtgcggtac       1020 agttacctcc aacaggacct gcctgacaac cccgagaggt tcaatctgtt tccctgtgtc      1080
ttgggctctc catgcttcat cgccgggaga cattattggg aggtagaggt gggagataaa      1140
gccaagtgga ccataggtgt ctgtgaagac tcagtgtgca gaaaaggtgg agtaacctca      1200
```

-continued

| | |
|---|---|
| gccccccaga atggattctg ggcagtgtct ttgtggtatg ggaaagaata ttgggctctt | 1260 |
| acctccccaa tgactgccct accctgcgg accccgctcc agcgggtggg gatttttcttg | 1320 |
| gactatgatg ctggtgaggt ctccttctac aacgtgacag agaggtgtca caccttcact | 1380 |
| ttctctcatg ctaccttttg tgggcctgtc cggccctact tcagtctgag ttactcggga | 1440 |
| gggaaaagtg cagctcctct gatcatctgc cccatgagtg ggatagatgg ttttctggc | 1500 |
| catgttggga atcatggtca ttccatggag acctccccctt ga | 1542 |

<210> SEQ ID NO 3
<211> LENGTH: 513
<212> TYPE: PRT
<213> ORGANISM: Homo sapiens

<400> SEQUENCE: 3

Met Ala Ser Gly Ser Val Ala Glu Cys Leu Gln Gln Glu Thr Thr Cys
1               5                   10                  15

Pro Val Cys Leu Gln Tyr Phe Ala Glu Pro Met Met Leu Asp Cys Gly
            20                  25                  30

His Asn Ile Cys Cys Ala Cys Leu Ala Arg Cys Trp Gly Thr Ala Glu
        35                  40                  45

Thr Asn Val Ser Cys Pro Gln Cys Arg Glu Thr Phe Pro Gln Arg His
    50                  55                  60

Met Arg Pro Asn Arg His Leu Ala Asn Val Thr Gln Leu Val Lys Gln
65                  70                  75                  80

Leu Arg Thr Glu Arg Pro Ser Gly Pro Gly Gly Glu Met Gly Val Cys
                85                  90                  95

Glu Lys His Arg Glu Pro Leu Lys Leu Tyr Cys Glu Glu Asp Gln Met
            100                 105                 110

Pro Ile Cys Val Val Cys Asp Arg Ser Arg Glu His Arg Gly His Ser
        115                 120                 125

Val Leu Pro Leu Glu Glu Ala Val Glu Gly Phe Lys Gly Gln Ile Gln
    130                 135                 140

Asn Gln Leu Asp His Leu Lys Arg Val Lys Asp Leu Lys Lys Arg Arg
145                 150                 155                 160

Arg Ala Gln Gly Glu Gln Ala Arg Ala Glu Leu Leu Ser Leu Thr Gln
                165                 170                 175

Met Glu Arg Glu Lys Ile Val Trp Glu Phe Gln Leu Tyr His Ser
            180                 185                 190

Leu Lys Glu His Glu Tyr Arg Leu Leu Ala Arg Leu Glu Glu Leu Asp
        195                 200                 205

Leu Ala Ile Tyr Asn Ser Ile Asn Gly Ala Ile Thr Gln Phe Ser Cys
    210                 215                 220

Asn Ile Ser His Leu Ser Ser Leu Ile Ala Gln Leu Glu Glu Lys Gln
225                 230                 235                 240

Gln Gln Pro Thr Arg Glu Leu Leu Gln Asp Ile Gly Asp Thr Leu Ser
                245                 250                 255

Arg Ala Glu Arg Ile Arg Ile Pro Glu Pro Trp Ile Thr Pro Pro Asp
            260                 265                 270

Leu Gln Glu Lys Ile His Ile Phe Ala Gln Lys Cys Leu Phe Leu Thr
        275                 280                 285

Glu Ser Leu Lys Gln Phe Thr Glu Lys Met Gln Ser Asp Met Glu Lys
    290                 295                 300

Ile Gln Glu Leu Arg Glu Ala Gln Leu Tyr Ser Val Asp Val Thr Leu
305                 310                 315                 320

```
Asp Pro Asp Thr Ala Tyr Pro Ser Leu Ile Leu Ser Asp Asn Leu Arg
                325                 330                 335
Gln Val Arg Tyr Ser Tyr Leu Gln Gln Asp Leu Pro Asp Asn Pro Glu
            340                 345                 350
Arg Phe Asn Leu Phe Pro Cys Val Leu Gly Ser Pro Cys Phe Ile Ala
        355                 360                 365
Gly Arg His Tyr Trp Glu Val Glu Val Gly Asp Lys Ala Lys Trp Thr
    370                 375                 380
Ile Gly Val Cys Glu Asp Ser Val Cys Arg Lys Gly Gly Val Thr Ser
385                 390                 395                 400
Ala Pro Gln Asn Gly Phe Trp Ala Val Ser Leu Trp Tyr Gly Lys Glu
                405                 410                 415
Tyr Trp Ala Leu Thr Ser Pro Met Thr Ala Leu Pro Leu Arg Thr Pro
            420                 425                 430
Leu Gln Arg Val Gly Ile Phe Leu Asp Tyr Asp Ala Gly Glu Val Ser
        435                 440                 445
Phe Tyr Asn Val Thr Glu Arg Cys His Thr Phe Thr Phe Ser His Ala
    450                 455                 460
Thr Phe Cys Gly Pro Val Arg Pro Tyr Phe Ser Leu Ser Tyr Ser Gly
465                 470                 475                 480
Gly Lys Ser Ala Ala Pro Leu Ile Ile Cys Pro Met Ser Gly Ile Asp
                485                 490                 495
Gly Phe Ser Gly His Val Gly Asn His Gly His Ser Met Glu Thr Ser
            500                 505                 510
Pro

<210> SEQ ID NO 4
<211> LENGTH: 19
<212> TYPE: RNA
<213> ORGANISM: Artificial Sequence
<220> FEATURE:
<223> OTHER INFORMATION: siRNA designed for inhibiting the expression of
      RFP gene

<400> SEQUENCE: 4
gaguuacucg ggagggaaa                                                  19

<210> SEQ ID NO 5
<211> LENGTH: 21
<212> TYPE: RNA
<213> ORGANISM: Artificial Sequence
<220> FEATURE:
<223> OTHER INFORMATION: siRNA designed for inhibiting the expression of
      RFP gene

<400> SEQUENCE: 5
aacucuuagg ccuaacccag a                                               21

<210> SEQ ID NO 6
<211> LENGTH: 21
<212> TYPE: RNA
<213> ORGANISM: Artificial Sequence
<220> FEATURE:
<223> OTHER INFORMATION: siRNA designed for inhibiting the expression of
      RFP gene

<400> SEQUENCE: 6
aagagaggcu caguuauacu c                                               21

<210> SEQ ID NO 7
<211> LENGTH: 19
```

```
<212> TYPE: RNA
<213> ORGANISM: Artificial Sequence
<220> FEATURE:
<223> OTHER INFORMATION: siRNA designed for inhibiting the expression of
      RFP gene

<400> SEQUENCE: 7
cccuaugagu gggauugau                                                    19

<210> SEQ ID NO 8
<211> LENGTH: 19
<212> TYPE: RNA
<213> ORGANISM: Artificial Sequence
<220> FEATURE:
<223> OTHER INFORMATION: siRNA designed for inhibiting the expression of
      RFP gene

<400> SEQUENCE: 8
gacucagugu gcagaaaag                                                    19

<210> SEQ ID NO 9
<211> LENGTH: 18
<212> TYPE: RNA
<213> ORGANISM: Artificial Sequence
<220> FEATURE:
<223> OTHER INFORMATION: siRNA designed for inhibiting the expression of
      RFP gene

<400> SEQUENCE: 9
agaaccagcu cgaccauu                                                     18

<210> SEQ ID NO 10
<211> LENGTH: 62
<212> TYPE: DNA
<213> ORGANISM: Artificial Sequence
<220> FEATURE:
<223> OTHER INFORMATION: DNA coding for shRFP designed for inhibiting
      the expression of RFP gene

<400> SEQUENCE: 10
gatcgagtta ctcgggaggg aaattcaaga gatttccctc ccgagtaact cttttttgga      60
aa                                                                      62

<210> SEQ ID NO 11
<211> LENGTH: 21
<212> TYPE: DNA
<213> ORGANISM: Artificial Sequence
<220> FEATURE:
<223> OTHER INFORMATION: primer specific to HDAC1

<400> SEQUENCE: 11
ctcctgtttt tttcaggctc c                                                 21

<210> SEQ ID NO 12
<211> LENGTH: 21
<212> TYPE: DNA
<213> ORGANISM: Artificial Sequence
<220> FEATURE:
<223> OTHER INFORMATION: primer specific to HDAC1

<400> SEQUENCE: 12
aggagaagac agacagaggg c                                                 21

<210> SEQ ID NO 13
<211> LENGTH: 20
<212> TYPE: DNA
<213> ORGANISM: Artificial Sequence
```

```
<220> FEATURE:
<223> OTHER INFORMATION: primer specific to RFP

<400> SEQUENCE: 13
tgctcgactg cggccataac                                              20

<210> SEQ ID NO 14
<211> LENGTH: 20
<212> TYPE: DNA
<213> ORGANISM: Artificial Sequence
<220> FEATURE:
<223> OTHER INFORMATION: primer specific to RFP

<400> SEQUENCE: 14
tcggtgcgca gctgctttac                                              20

<210> SEQ ID NO 15
<211> LENGTH: 21
<212> TYPE: DNA
<213> ORGANISM: Artificial Sequence
<220> FEATURE:
<223> OTHER INFORMATION: primer specific to TBP-2

<400> SEQUENCE: 15
tgagatggtg atcatgagac c                                            21

<210> SEQ ID NO 16
<211> LENGTH: 21
<212> TYPE: DNA
<213> ORGANISM: Artificial Sequence
<220> FEATURE:
<223> OTHER INFORMATION: primer specific to TBP-2

<400> SEQUENCE: 16
gtattgacat ccaccagatc c                                            21

<210> SEQ ID NO 17
<211> LENGTH: 21
<212> TYPE: DNA
<213> ORGANISM: Artificial Sequence
<220> FEATURE:
<223> OTHER INFORMATION: primer specific to GAPDH

<400> SEQUENCE: 17
gaaggtgaag gtcggagtca a                                            21

<210> SEQ ID NO 18
<211> LENGTH: 22
<212> TYPE: DNA
<213> ORGANISM: Artificial Sequence
<220> FEATURE:
<223> OTHER INFORMATION: primer specific to  GAPDH

<400> SEQUENCE: 18
gagatgatga ccctttggc tc                                            22
```

POTENTIATOR OF ACTIVITY OF ANTI-CANCER AGENT AND USE THEREOF, AND BIOMARKER FOR PREDICTION OF PROGNOSIS IN CANCER PATIENT AND USE THEREOF

TECHNICAL FIELD

The present invention relates to an agent for enhancing the action of anticancer drugs and use thereof, as well as a biomarker for estimating prognosis in cancer patients and use thereof, and the like.

BACKGROUND ART

Histone deacetylases (HDACs) are involved in the carcinogenesis by regulating cell proliferation, differentiation, and survival (Non Patent Literature 1 and 2). The inhibitors of HDACs (HDACi) have been shown to exhibit profound synergistic effects for cancer treatment when combined with other anticancer drugs (Non Patent Literature 2 and 3). The molecular mechanisms how this synergy is induced following the addition of HDACi, however, have not been fully understood.

Systematic in vitro studies revealed that HDACi can induce cell growth arrest, terminal differentiation, cell death and/or inhibition of angiogenesis in transformed cells without affecting normal cells (Non Patent Literature 2, 3 and 5). Based on these in vitro findings, several HDACi are currently being tested in clinical trials and one such inhibitor suberoylanilide hydroxamic acid (SAHA) has been approved by FDA for cutaneous T-cell lymphoma treatment (Non Patent Literature 4 and 5). HDACi have also shown synergistic or additive effects with a wide variety of anti-cancer reagents (Non Patent Literature 2 and 4). In addition, it is known that cytotoxicity of chemotherapeutic agents, including cisplatin, etoposide, 5-FU, and doxorubicin, is achieved in part by generation of reactive oxygen species (ROS) (Non Patent Literature 6 to 9). Consistent with these findings, alteration of antioxidant and its related gene expression modulate the resistance to chemotherapeutic drugs probably through its ROS scavenging ability (Non Patent Literature 10 to 13). This fact supports the findings that the induction of ROS by the chemotherapeutic drugs is important for cytotoxicity.

Citation List

[Non Patent Literature]

[Non Patent Literature 1] Yang, X J. and Seto, E. The Rpd3/Hda1 family of lysine deacetylases: from bacteria and yeast to mice and men. Nat Rev Mol Cell Biol. 9(3):206-18 (2008)

[Non Patent Literature 2] Bolden, J E., Peart, M J. and Johnstone, R W. Anticancer activities of histone deacetylase inhibitors. Nat Rev Drug Discov. 5(9):769-84 (2006).

[Non Patent Literature 3] Minucci, S. and Pelicci, P G Histone deacetylase inhibitors and the promise of epigenetic (and more) treatments for cancer. Nature Reviews Cancer. 6(1):38-51 (2006).

[Non Patent Literature 4] Xu, W S., Parmigiani, R B. and Marks, P A. Histone deacetylase inhibitors: molecular mechanisms of action. Oncogene. 26(37):5541-52 (2007).

[Non Patent Literature 5] Marks, P A. and Breslow, R. Dimethyl sulfoxide to vorinostat: development of this histone deacetylase inhibitor as an anticancer drug. Nature Biotechnology. 25(1):84-90 (2007).

[Non Patent Literature 6] Miyajima, A. et al. Role of reactive oxygen species in cis-dichlorodiammineplatinum-induced cytotoxicity on bladder cancer cells. Br J Cancer. 76(2):206-10 (1997).

[Non Patent Literature 7] Kurosu, T., Fukuda, T., Miki, T. and Miura, O. BCL6 overexpression prevents increase in reactive oxygen species and inhibits apoptosis induced by chemotherapeutic reagents in B-cell lymphoma cells. Oncogene. 22(29):4459-68 (2003).

[Non Patent Literature 8] Hwang, I T. et al. Drug resistance to 5-FU linked to reactive oxygen species modulator 1. Biochem Biophys Res Commun. 359(2):304-10 (2007).

[Non Patent Literature 9] Ravid, A. et al. 1,25-Dihydroxyvitamin D3 enhances the susceptibility of breast cancer cells to doxorubicin-induced oxidative damage. Cancer Res. 59(4):862-7 (1999).

[Non Patent Literature 10] Godwin, A K. et al. High resistance to cisplatin in human ovarian cancer cell lines is associated with marked increase of glutathione synthesis. Proc Natl Acad Sci USA. 89(7):3070-4 (1992).

[Non Patent Literature 11] Yokomizo, A. et al. Cellular levels of thioredoxin associated with drug sensitivity to cisplatin, mitomycin C, doxorubicin and etoposide. Cancer Res. 55(19):4293-6 (1995).

[Non Patent Literature 12] Sasada, T. et al. Redox control of resistance to cis-diamminedichloroplatinum (II) (CDDP): protective effect of human thioredoxin against CDDP-induced cytotoxicity. J Clin Invest. 97(10):2268-76 (1996).

[Non Patent Literature 13] Powis, G and Kirkpatrick, D L. Thioredoxin signaling as a target for cancer therapy. Curr Opin Pharmacol. 7(4):392-7 (2007).

[Non Patent Literature 14] Halkidou K, Gaughan L, Cook S, Leung H Y, Neal D E, Robson C N. (2004). Upregulation and nuclear recruitment of HDAC1 in hormone refractory prostate cancer. Prostate 59: 177-189

[Non Patent Literature 15] Glozak M A, Seto E. (2007). Histone deacetylases and cancer. Oncogene 26: 5420-5432

[Non Patent Literature 16] Takahashi M, Inaguma Y, Hiai H, Hirose F. (1988). Developmentally regulated expression of a human "finger"-containing gene encoded by the 5' half of the ret transforming gene. Mol Cell Biol. 4:1853-6

[Non Patent Literature 17] Tezel, G et al. M. (1999). Different nuclear/cytoplasmic distributions of RET finger protein in different cell types. Pathol. Int. 49: 881-886

[Non Patent Literature 18] Takahashi, M. and Cooper, G. M.: ret transforming gene encodes a fusion protein homologous to tyrosine kinases. Mol. Cell. Biol. 7, 1378-1385 (1987)

[Non Patent Literature 19] Shimono, Y., Murakami, H., Hasegawa, Y. and Takahashi, M.: RFP is a transcriptional repressor and interacts with enhancer of polycomb that has dual transcriptional functions. J. Biol Chem. 275: 39411-39419. (2000)

[Non Patent Literature 20] Shimono, Y., Murakami, H., Kawai, K., Wade, P. A., Shimokata, K. and Takahashi, M.: Mi-2 associates with BRG1 and RET finger protein at the distinct regions with transcriptional activating and repressing abilities. J. Biol. Chem. 278: 51638-51645 (2003)

[Non Patent Literature 21] Shimono, K., Shimono, Y., Shimokata, K., Ishiguro, N., and Takahashi, M.: Microspherule protein 1, Mi-2β, and RET finger protein associate in the nucleolus and up-regulate ribosomal gene transcription. J. Biol. Chem. 280: 39436-39447 (2005)

DISCLOSURE OF INVENTION

[Technical Problem]

A plurality of anticancer drugs are often used in combination for cancer therapy. Although combined use of anticancer drugs is carried out in order to improve the therapeutic effect, it may sometimes bring about serious adverse effects. This is because many of currently used anticancer drugs target cells that proliferate rapidly and therefore exert cytotoxicity in normal cells other than cancer cells.

Under the above-mentioned background, an object of the present invention is to provide means for enhancing the action of an anticancer drug, or to provide a biomarker useful for grasping prognosis in cancer patients and the use thereof, and thereby contributing to improving clinical outcomes of cancer therapy.

[Solution to Problem]

To date, it has been revealed that HDACi changes the expression of Thioredoxin and TBP-2 regulating an oxidation state in cells. From the viewpoint of this fact, the present inventors have made a hypothesis that HDACi regulates the antioxidation mechanism in cells, thereby allowing cancer cells to be sensitive to an anticancer drug. In order to verify the hypothesis, the present inventors have focused on HDAC1 and RFP (RET finger protein) and keenly investigated. HDAC1 has characteristics that: (1) it is found to be highly expressed in human tumors, and (2) it regulates proliferation, differentiation, and survival of cells (Halkidou K, Gaughan L, Cook S, Leung H Y, Neal D E, Robson C N. (2004). Upregulation and nuclear recruitment of HDAC1 in hormone refractory prostate cancer. Prostate 59: 177-189 (Non-patent Document 14); Glozak M A, Seto E. (2007). Histone deacetylases and cancer. Oncogene 26: 5420-5432 (Non-patent Document 15)). RFP has characteristics that: (1) it is highly expressed in a cancer cell line; (2) its expression in a living body is localized (Takahashi M, Inaguma Y, Hiai H, Hirose F. (1988). Developmentally regulated expression of a human "finger"-containing gene encoded by the 5' half of the ret transforming gene. Mol Cell Biol. 4:1853-6 (Non-patent Document 16); Tezel, G et al. M. (1999). Different nuclear/cytoplasmic distributions of RET finger protein in different cell types. Pathol. Int. 49: 881-886 (Non-patent Document 17)); and (3) its knockout mouse does not exhibit a phenotype of serious conditions (unpublished data). As a result, it has been revealed that HDAC1 downregulates the expression of Thioredoxin Binding Protein-2 (TBP-2), thereby accelerating the resistance of cancer cells to oxidative stress. Furthermore, it has been found that HDAC1 is recruited to a promoter of a TBP-2 gene by a protein complex composed of RFP and a transcription factor NF-Y. Furthermore, the suppression of expression of REP using RNAi causes disintegration of the protein complex, resulting in remarkably increasing the sensitivity of cancer cells to cisplatin (which is also an anticancer drug, an oxidative stress inducer). These facts mean that RFP is an important regulation factor that allows cancer cells to gain resistance to an anticancer drug, and suggest that suppression of the expression or the function of RFP enhances the action of an anticancer drug to thus improve clinical outcomes of cancer therapy.

On the other hand, it has been revealed that high expression of RFP correlates to the decrease in the expression of TBP-2 in human colon carcinoma or poor prognosis in colon carcinoma patients. This supports the effectiveness of treatment strategy of suppressing the expression or the function of RFP when anticancer drugs are used, and means that the resistance to anticancer drugs can be determined by examining the expression level of RFP in cancer cells and the determination results are useful information that contributes to determining treatment policies (selection of effective treatment method, and the like), making prognosis better, and improving the quality of life (QOL) of patients. As a result of a further investigation, it has been revealed that RFP expression correlates with poor prognosis in endometrial cancer patients. Interestingly, findings have been obtained: when high expression of RFP is observed, employing more aggressive operations leads to the improvement of prognosis. As mentioned above, it is shown that RFP is useful as a biomarker (indicator) for estimating prognosis in cancer patients. In particular, in endometrial cancer, it is suggested that RFP expression is a useful indicator in determining an operative method.

The present invention is mainly based on the above-mentioned findings and results and includes the following.

[1] An action enhancing agent of an anticancer drug having an oxidative stress-inducing ability, including a compound, as an active ingredient, for suppressing expression of a RFP (RET finger protein) gene or action of RFP.

[2] The action enhancing agent according to [1], wherein the compound is selected from the group consisting of the following (a) to (d):

(a) siRNA targeting the RFP gene;

(b) a nucleic acid construct for generating the siRNA targeting the RFP gene in a cell;

(c) an antisense nucleic acid targeting a transcriptional product of the RFP gene; and (d) a ribozyme targeting a transcriptional product of the RFP gene.

[3] The action enhancing agent according to [1] or [2], which is used in combination with an anticancer drug having an oxidative stress-inducing ability.

[4] A method for enhancing action of an anticancer drug having an oxidative stress-inducing ability, the method including a step of suppressing expression of a RFP gene or action of RFP in a target cell.

[5] A method for treating a cancer, the method including:

a step of administering the action enhancing agent according to [1] or [2]; and a step of administering an anticancer drug having an oxidative stress-inducing ability.

[6] A method for testing resistance to an anticancer drug, the method including:

a step of examining an expression amount of RFP in a cancer cell separated from a living body; and a step of determining resistance of the cancer cell to an anticancer drug having an oxidative stress-inducing ability based on the result of the step.

[7] A biomarker for estimating prognosis in a cancer patient, which includes RFP.

[8] The biomarker for estimating prognosis according to [7], wherein the cancer is colon carcinoma or endometrial cancer.

[9] A method for estimating prognosis in a cancer patient, wherein an expression amount of RFP in a cancer cell separated from a cancer patient is used as an indicator.

[10] The method for estimating prognosis according to [9], wherein when an expression amount of RFP in a cell is large, poor prognosis is indicated.

[11] The method for estimating prognosis according to [9] or [10], wherein the cancer is colon carcinoma or endometrial cancer.

[12] A reagent for estimating prognosis in a cancer patient, including an anti-RFP antibody.

[13] The reagent for estimating prognosis according to [12], wherein the cancer is colon carcinoma or endometrial cancer.

[14] A kit for estimating prognosis in a cancer patient, including a reagent according to [12] or [13].

[15] The kit for estimating prognosis according to [14], wherein the cancer is colon carcinoma or endometrial cancer.

Advantageous Effects of Invention

Combined use of an action enhancing agent of the present invention improves action of anticancer drugs such as cisplatin having an oxidative stress-inducing ability. This can reduce the amount of an anticancer drug to be used or types of the anticancer drugs (in the case where two or more types of anticancer drugs are used in combination). Furthermore, clinical outcomes of therapy can be improved.

Figure 1:
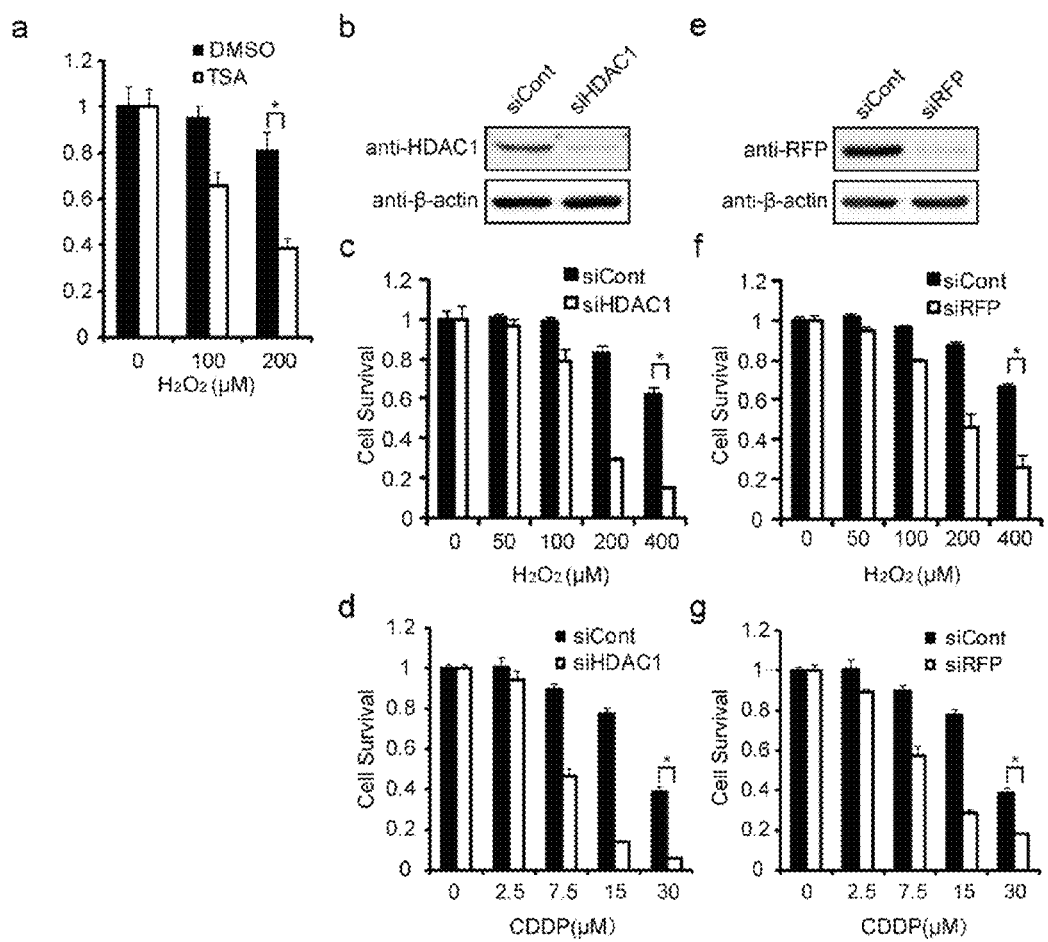
[FIG. 1] Functional association between HDAC1 and RFP. (a) Effect of HDACi treatment on cellular sensitivity to oxidative stress. HeLa cells were treated for 10 h with indicated doses of $H_2O_2$ with or without pretreatment of TSA (500 nM) for 3 h. Cell viability was measured by WST-1 assay and cell survival index of non-treatment group was defined as 1. (b) siRNA-mediated knockdown of endogenous HDAC1 in HeLa cells. Total cell lysates from HeLa cells transfected with either control or HDAC1 siRNAs were analysed by western blotting with anti-HDAC1. Anti-β-actin was used as loading control. Suppression of expression of HDAC1 was observed in cells into which siHDAC1 had been introduced. (c), (d) HeLa cells transfected with control or HDAC1 siRNA, and treated with indicated doses of $H_2O_2$ (10 h) in c and cisplatin (24 h) in d. Cell viability was measured and calculated as described in a. In the knockdown cells of HDAC1, the decreasing degree of the cell survival index is larger in the treated cells than in control. (e) siRNA-mediated knockdown of endogenous RFP in HeLa cells. Total cell lysates from HeLa cells transfected with either control or RFP siRNAs were analysed by western blotting with anti-RFP and anti-β-actin antibodies. Suppression of expression of RFP was observed in cells into which siRFP had been introduced. (f), (g) HeLa cells transfected with control or RFP siRNA, and treated with indicated doses of $H_2O_2$ (10 h) in f and cisplatin (24 h) in g. Cell viability was measured and calculated as described in a. In the knockdown cells of RFP, the decreasing degree of the cell survival index is larger in the treated cells than in the control.

DESCRIPTION OF EMBODIMENTS (Action Enhancing Agent of Anticancer Drugs and Use Thereof)

The first aspect of the present invention relates to an action enhancing agent of anticancer drugs (hereinafter, referred to as an "agent of the present invention"). The agent of the present invention enhances action of anticancer drugs having the oxidative stress-inducing ability. In other words, the agent of the present invention enhances action of anticancer drugs whose efficacy is weakened or lost when the oxidative stress resistance is accelerated in target cancer cells. In the present invention, "enhance action of anticancer drugs" or "action enhancement of anticancer drugs" refers to enhancing anticancer action of anticancer drugs. When the agent of the present invention is used in combination with an anticancer drug, clinical outcomes of cancer therapy can be improved. The term "improvement of clinical outcomes of therapy" herein includes: (1) increase in therapeutic effect; (2) improvement of effectiveness or efficiency; and (3) reduction or avoidance of adverse effect (according to the present invention, at least one of them is achieved). Examples of anticancer drugs include platinum formulation such as cisplatin, carboplatin, and oxaliplatin, cyclophosphamide, fluorouracil (5-FU), etoposide, doxorubicin, bleomycin, and mitomycin.

As a result of the investigation by the present inventors, it has been revealed that HDAC1 accelerates the resistance of cancer cells to the oxidative stress by downregulating the expression of Thioredoxin-binding protein 2 (TBP-2). In order to prevent the action of HDAC1 and to increase the sensitivity of cancer cells to anticancer drugs, the agent of the present invention targets RFP that has been revealed to be necessary for recruiting HDAC1 to the TBP-2 gene promoter. In detail, the agent of the present invention includes, as an active ingredient, a compound for suppressing expression of a RFP gene or action of RFP. Note here that two terms "suppress" and "prevent" have the same meaning and are often used interchangeably. Then, the present specification uses "suppress" unless both terms need to be distinguished from each other from its context.

RFP is a nuclear protein having a ring finger structure, which forms fusion protein with RET and then is activated as cancer protein (Takahashi, M. and Cooper, G M.: ret transforming gene encodes a fusion protein homologous to tyrosine kinases. Mol. Cell. Biol. 7, 1378-1385 (1987) (Non-patent Document 18); Non-patent Document 16). RFP has a strong transcriptional repressor activity, and interacts with various nuclear proteins (Shimono, Y., Murakami, H., Hasegawa, Y. and Takahashi, M.: RFP is a transcriptional repressor and interacts with enhancer of polycomb that has dual transcriptional functions. J. Biol Chem. 275: 39411-39419. (2000) (Non-patent Document 19); Shimono, Y., Murakami, H., Kawai, K., Wade, P. A., Shimokata, K. and Takahashi, M.: Mi-2 associates with BRG1 and RET finger protein at the distinct regions with transcriptional activating and repressing abilities. J. Biol. Chem. 278: 51638-51645 (2003) (Non-patent Document 20); Shimono, K., Shimono, Y, Shimokata, K., Ishiguro, N., and Takahashi, M.: Microspherule protein 1, Mi-2β, and RET finger protein associate in the nucleolus and up-regulate ribosomal gene transcription. J. Biol. Chem. 280: 39436-39447 (2005) (Non-patent Document 21)). It was reported that RFP highly expresses in a cancer cell line. However, an expression state of RFP in cancer tissue has not been clarified. The sequence of a RFP gene (SEQ ID NO: 1), the sequence of mRNA of RFP (SEQ ID NO: 2), and the amino acid sequence of RFP (SEQ ID NO: 3) are shown in the Sequence List. As mentioned above, since the knockout mouse targeting RFP does not show a phenotype of serious conditions, targeting RFP is preferable from the viewpoint of safety. Furthermore, since high expression is observed in a plurality of types of human tumors or cultured cell lines derived from most of the examined tumors (unpublished data and Non-patent Document 16), it is expected that the action can be exhibited in wide range of tumors.

The compound as an active ingredient for suppressing expression of a RFP gene in the present invention is a compound for suppressing an expression process of the RFP gene (including transcription, post-transcriptional regulation, translation, and post-translational regulation). Examples of the compound follow. The "suppression of expression" in the present invention may be transient suppression or constitutive suppression.

(a) siRNA targeting the RFP gene;
(b) a nucleic acid construct for generating the siRNA targeting the RFP gene in a cell;
(c) an antisense nucleic acid targeting a transcriptional product of the RFP gene; and
(d) a ribozyme targeting a transcriptional product of the RFP gene.

The above-mentioned (a) and (b) are compounds used for so-called expression suppression by RNAi (RNA interference). In other words, an agent of the present invention including the compound of the above-mentioned (a) or (b) as an active ingredient can suppress expression of RFP by RNAi. RNAi is a process of a sequence-specific post-transcriptional gene suppression that can be induced in the eukaryote. For RNAi with respect to mammalian cells, short double strand RNA (siRNA) of the sequence corresponding to the sequence of the target mRNA is used. In general, the siRNA has 21 to 23 base pairs. It is known that mammalian cells have two routes (a sequence-specific route and a sequence-nonspecific route) affected by double strand RNA (dsRNA). In the sequence-specific route, relatively long dsRNA is divided into short interference RNAs (i.e., siRNAs). On the other hand, it is thought that a sequence-non-specific route can be elicited by arbitrary dsRNA regardless of the sequence as long as it has a predetermined length or longer. In this route, dsRNA activates two enzymes, that is, PKR, which becomes an active form and stops all synthesis of proteins by phosphorylating the translation initiation factor eIF2, and 2',5' oligoadenylate synthetase, which is involved in the synthesis of an RNAase L activated molecule. In order to minimize the advance of this nonspecific route, it is preferable to use double strand RNA (siRNA) including shorter than about 30 base pairs (see, for example, Hunter et al. (1975) J Biol Chem 250: 409-17; Manche et al. (1992) Mol Cell Biol 12: 5239-48; Minks et al. (1979) J Biol Chem 254: 10180-3; and Elbashir et al. (2001) Nature 411: 494-8).

In order to generate target-specific RNAi, siRNA composed of a sense RNA homologous to a part of a mRNA sequence of a target gene and an antisense RNA complementary to the sense RNA may be introduced into a cell, or may be allowed to be expressed in a cell. The above-mentioned (a) is a compound corresponding to the former method, and the above-mentioned (b) is a compound corresponding to the latter method.

The siRNA targeting a target gene (a RFP gene in the present invention) is generally double strand RNA in which a sense RNA composed of a sequence homologous to a continuous region in the sequence of mRNA in the gene and an antisense RNA composed of a sequence complementary to the sense sequence hybridize to each other. Herein, the length of the "continuous region" is usually 15 to 30 nucleotides, preferably 18 to 23 nucleotides, and more preferably 19 to 21 nucleotides.

Double strand RNA having an overhang of several nucleotides at the terminal is known to exhibit a high RNAi effect. Then, also in the present invention, it is preferable that siRNA having such a structure is employed. The length of the nucleotides constituting the overhang is not particularly limited, but it is preferably two nucleotides (for example, TT and UU).

siRNA composed of modified RNA may be used. Herein, examples of the modification include phosphorothioation, use of a modified base (for example, a fluorescent labeled base), and the like.

Design and preparation of siRNA can be carried out by a conventional method. Designing of siRNA is usually carried out by using a sequence (continuous sequence) peculiar to a target sequence. Note here that program and algorithm for selecting an appropriate target sequence have been developed.

Examples of the sequences of siRNA targeting a RFP gene follow.

5'-GAGTTACTCGGGAGGGAAA-3' (SEQ ID NO: 4. A sequence used in the below-mentioned Example)

5'-AACTCTTAGGCCTAACCCAGA-3' (SEQ ID NO: 5. See, Krutzfeldt M, Ellis M, Weekes D B, Bull J J, Eilers M, Vivanco M D, Sellers W R, Mittnacht S. (2005). Selective ablation of retinoblastoma protein function by the RET finger protein. Mol Cell. 18(2):213-24.)

5'-AAGAGAGGCUCAGUUAUACUC-3' (SEQ ID NO: 6. See, Krutzfeldt M, Ellis M, Weekes D B, Bull J J, Eilers M, Vivanco M D, Sellers W R, Mittnacht S. (2005). Selective ablation of retinoblastoma protein function by the RET finger protein. Mol Cell. 18(2):213-24.)

5'-CCCUAUGAGUGGGAUUGAU-3' (SEQ ID NO: 7. See, Fukushige S, Kondo E, Gu Z, Suzuki H, Horii A.(2006). RET finger protein enhances MBD2- and MBD4-dependent transcriptional repression. Biochem Biophys Res Commun. 351(1): 85-92. Epub 2006 Oct. 10.)

5'-GACTCAGTGTGCAGAAAAG-3' (SEQ ID NO: 8. See, Zha J, Han K J, Xu L G, He W, Zhou Q, Chen D, Zhai Z, Shu H B.(2006). The Ret finger protein inhibits signaling mediated by the noncanonical and canonical IkappaB kinase family members. J Immunol. January 15; 176(2):1072-80.)

5'-AGAACCAGCTCGACCATT-3' (SEQ ID NO: 9. See, Townson S M, Kang K, Lee A V, Oesterreich S.(2006). Novel role of the RET finger protein in estrogen receptor-mediated transcription in MCF-7 cells. Biochem Biophys Res Commun. October 20; 349(2):540-8. Epub 2006 Aug. 22.)

The "nucleic acid construct for generating the siRNA targeting the RFP gene in a cell" in the above (b) refers to a nucleic acid molecule that generates desired siRNA (siRNA inducing RNAi with respect to a target gene) in a process in a cell when it is introduced into a cell. An example of the nucleic acid construct is shRNA (short hairpin RNA). The shRNA has a structure (hairpin structure) in which a sense RNA and an antisense RNA are linked to each other via a loop structure part. The loop structure part is cleaved into a double strand siRNA in a cell, thus bringing about an RNAi effect. The length of the loop structure part is not particularly limited, but it is usually 3 to 23 nucleotides.

Another example of the nucleic acid construct is a vector capable of expressing a desired siRNA. Examples of such a vector may include a vector expressing shRNA that is converted into siRNA in a later process (a vector in which a sequence encoding shRNA is inserted) (which is referred to as a stem loop type or a short hairpin type), and a vector that expresses a sense RNA and an antisense RNA independently (which is referred to as a tandem type). These vectors can be produced according to a conventional method by a person skilled in the art (see, for example, Brummelkamp T R et al. (2002) Science 296: 550-553; Lee N S et al. (2001) Nature Biotechnology 19:500-505; Miyagishi M & Taira K (2002) Nature Biotechnology 19:497-500; Paddison P J et al.(2002) Proc. Natl. Acad. Sci. USA 99:1443-1448; Paul C P et al. (2002) Nature Biotechnology 19 :505-508; Sui G et al.(2002) Proc Natl Acad Sci USA 99(8):5515-5520; Paddison P J et al.(2002) Genes Dev. 16:948-958). At present, various vectors for RNAi are available. The vector of the present invention may be constructed by using such well-known vectors. In this case, an insert DNA encoding a desired RNA (for example, shRNA) is prepared, and then inserted into a cloning site of the vector to form an RNAi expression vector. Specific examples of the shRNA are shown in SEQ ID NO: 10 in the sequence listing. SEQ ID NO: 10 is a sequence of a single strand oligonucleotide (sense strand) encoding a shRNA targeting RFP.

Note here that the origin and structure of the vector are not limited as long as it has a function of generating siRNA that exhibits RNAi with respect to a target gene. Therefor, various viral vectors (for example, an adenovirus vector, an adeno-associated virus vector, a retrovirus vector, a lentivirus vector, a herpes virus vector, a Sendai virus vector, etc), and non-viral vectors (for example, liposome, positively charged liposome, etc.), and the like, can be used. Examples of a promoter that can be used for a vector may include a U6 promoter, an H1 promoter, and a tRNA promoter. Such promoters are RNA polymerase III type promoters, and expected to have high expression efficiency.

The above-mentioned (c) is a compound used for suppressing the expression by an antisense method. In other words, with an agent of the present invention including the compound of the above-mentioned (c) as an active ingredient, the expression of RFP can be suppressed by the antisense method. In the case where the expression inhibition by the antisense method is carried out, for example, when transcription is carried out in the target cell, an antisense construct for generating RNA that is complementary to a portion specific to mRNA encoding RFP is used. Such an antisense construct is introduced into the target cell, for example, in a form of an expression plasmid. On the other hand, when it is introduced into the target cell as the antisense construct, it is possible to employ an oligonucleotide probe that is hybridized with mRNA or genome DNA sequence encoding RFP and inhibits the expression thereof. As such an oligonucleotide probe, one having a resistance to endogenous nuclease such as exonuclease and/or endonuclease is preferably used.

When a DNA molecule is used as an antisense nucleic acid, it is preferable that oligodeoxyribonucleotide derived from a region including a translation initiation site (for example, a region from −10 to +10) of mRNA encoding RFP is used.

It is preferable that the complementation between the antisense nucleic acid and the target nucleic acid is strict. However, some mismatch may be accepted. The hybridization performance of the antisense nucleic acid with respect to the target nucleic acid is generally dependent upon both the degree of complementation and the length of both nucleic acids. In general, as the antisense nucleic acid to be used is longer, even if the number of mismatch is increased, stable two heavy chains (or three heavy chains) can be formed between the antisense nucleic acid and the target nucleic acid. A person skilled in the art can confirm the degree of acceptable mismatch by using a standard technique.

The antisense nucleic acid may be DNA, RNA or a chimera mixture thereof, or derivative or modified type thereof. Furthermore, it may be single stranded or double stranded. By modifying a base portion, a sugar portion or a skeleton portion of phosphoric acid, the stability and hybridization performance and the like of the antisense nucleic acid can be improved. Furthermore, to the antisense nucleic acid, materials for urging the cell membrane transportation (see, for example, Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988) or materials for enhancing the affinity with respect to certain cells may be added.

The antisense nucleic acid can be synthesized by a conventional method, for example, by using commercially available automated DNA synthesizer (for example, Applied Biosystems, and the like). For producing the modulated product or derivative of nucleic acid, see, for example, Stein et al.

(1988), Nucl. Acids Res. 16:3209, or Sarin et al., (1988), Proc. Natl. Acad. Sci. U.S.A. 85:7448-7451.

In order to enhance the action of antisense nucleic acid in the target cells, a strong promoter such as pol II and pol III can be used. That is to say, if a construct including antisense nucleic acid disposed under control of such a promoter is introduced into the target cell, it is possible to secure the transcription of sufficient amount of antisense nucleic acid by the action of the promoter.

The antisense nucleic acid can be expressed by using any promoters (inducible promoters or constitutive promoters) known to function in the mammalian cells (preferably, human cells). For example, promoters such as a SV40 initial promoter region (Bernoist and Chambon, 1981, Nature 290:304-310), a promoter derived from the 3'-terminal region of Rous sarcoma virus (Yamamoto et al., 1980, Cell 22:787-797), a Herpetic Thymidine Kinase promoter (Wagner et al., 1981, Proc. Natl. Acad. Sci. U.S.A. 78: 1441-1445), and the like, can be used.

One embodiment of the present invention uses suppression of expression by a ribozyme (in the case of the compound of the above-mentioned (d)). By using ribozyme for cleaving mRNA at the site specific recognition sequence, it may be possible to destroy target mRNA. Preferably, however, a hammerhead ribozyme is used. A method for constructing the hammerhead ribozyme can be referred to, for example, Haseloff and Gerlach, 1988, Nature, 334: 585-591.

Similar to the case of using the antisense method, for example, for the purpose of improving the stability and target performance, ribozyme may be constructed by using a modified oligonucleotide. In order to produce an effective amount of ribozyme in the target cell, for example, it is preferable to use a nucleic acid construct in which DNA encoding the ribozyme is disposed under the control of a strong promoter (for example, pol II and pol III).

In one embodiment of the present invention, a compound suppressing the action of RFP is used as an active ingredient. As a result of the investigation by the present inventors (see the below-mentioned Examples), it has been revealed that RFP is involved in regulation of the oxidative stress sensitivity by HDAC1 via the physical and functional interaction between RFP and HDAC1. Based on the findings, drugs of this embodiment suppress the interaction between RFP and HDAC1 so as to enhance the action of anticancer drugs. The types of the compounds are not particularly limited as long as they can suppress the interaction between RFP and HDAC1. As a result of the investigation by the present inventors, it has been revealed that the N-terminal side of HFAC1 binds to a coiled-coil domain and an Rfp domain of the RFP. Therefore, any compounds that can inhibit this binding may be used as an active ingredient. For example, an antibody that can specifically bind to the coiled coil domain or the Rfp domain of the RFP can be employed. Types or forms of the antibodies are not particularly limited. Any of a polyclonal antibody, an oligoclonal antibody and a monoclonal antibody may be used. Furthermore, a chimeric antibody (for example, chimera of human and mouse), a humanized antibody, a human antibody, and the like, may be used. In addition, antibody fragments such as Fab, Fab', F(ab')$_2$, scFv, and dsFv can be used.

The antibody as an active ingredient can be prepared by an immunologic procedure using HDAC1 or RFP or a part thereof (preferably, a site involved in the interaction) as an antigen, a phage display technique, a ribosome display method, and the like.

An active ingredient may be a compound binding competitively to RFP with respect to the N-terminal side of HDAC1. Examples of such compounds include coiled coil domain-like polypeptide and Rfp domain-like polypeptide of RFP.

Note here that instead of using an antibody itself as an active ingredient, a vector that can express a desirable antibody in a cell may be used as an active ingredient. The same is true to compounds other than an antibody.

The agent of the present invention can be formulated according to a conventional method. In formulation, other ingredients acceptable for formulation (for example, carriers, vehicles, disintegrating agents, buffer agents, emulsifying agents, suspending agents, soothing agents, stabilizers, preservatives, antiseptics, physiological saline) can be contained. An example of the vehicle may include lactose, starch, sorbitol, D-mannitol, sucrose, and the like. An example of the disintegrating agents may include starch, carboxymethyl cellulose, calcium carbonate, and the like. An example of the buffer agent may include phosphate, citrate, acetate, and the like. An example of the emulsifying agent may include gum Arabic, alginate sodium, tragacanth, and the like. An example of the suspending agent may include glyceryl monostearate, aluminum monostearate, methylcellulose, carboxymethyl cellulose, hydroxymethyl cellulose, sodium lauryl sulfate, and the like. An example of the soothing agent may include benzyl alcohol, chlorobutanol, sorbitol, and the like. An example of the stabilizer may include propylene glycol, diethylene sulfite, ascorbic acid, and the like. An example of the preservative may include phenol, benzalkonium chloride, benzyl alcohol, chlorobutanol, methylparaben, and the like. An example of the antiseptic may include benzalkonium chloride, parahydroxybenzoate, chlorobutanol, and the like.

The dosage form in the formulation is not particularly limited. An example of the dosage form may include tablet, powdered drug, fine subtilae, granule, capsules, syrup, injectable drug, external preparation, and suppository.

The agent of the present invention contains an active ingredient is contained in an amount necessary to obtain an expected therapeutic effect (or prophylaxis effect) (that is, a therapeutically effective amount). The amount of the active ingredient in the agent of the present invention is set to, for example, in the range from about 0.1 wt. % to about 95 wt. % to achieve a desirable dosage amount although it is different depending upon the dosage forms.

The agent of the present invention can be administered to a subject by oral administration or parenteral administration (intravenous, intra-arterial, subcutaneous, intracutaneous, intramuscular, intraperitoneal injection, transdermal, transnasal, transmucosal, and the like) depending upon the dosage form. These administration routes are not exclusive, and two or more of any selected routes can be used (for example, intravenous injection is carried out concurrently with or a predetermined time has passed after oral administration).

When a nucleic acid construct is an active ingredient (for example, an embodiment using RNAi), not only in vivo administration but also ex vivo administration can be employed.

The subject to which the agent of the present invention is administered is not particularly limited, and includes human and non-human mammalians (including pet animals, domestic animal, laboratory animals, and the like. Specific examples include mouse, rat, guinea pig, hamster, monkey, cow, pig, goat, sheep, dog, cat, chicken, quail, and the like). In the preferable embodiment, agent of the present invention is applied to human.

The dosage amount will vary depending on the symptoms, age, sex, body weight, and the like, of patients, but a person skilled in the art can set an appropriate dosage amount. For setting the administration schedule, conditions of a patient, efficacy duration time of the agent, and the like, can be considered.

The agent of the present invention is used in combination with anticancer drugs. That is to say, the agent of the present invention and the anticancer drug are used in combination. Typically, the agent of the present invention and a predetermined anticancer drug are prepared, and both are administered to a subject. In this case, they are to be administered (applied) to the subject concurrently or at an interval of a predetermined time. Herein, the "concurrent" does not require strict concurrence. Therefore, the concept of the "concurrent" includes not only administering both agents after they are mixed with each other, that is, a case in which the administration of both agents are carried out without time difference, but also the case in which immediately after one agent is administered, the other is administered, that is, the administration of both agents are carried out without substantial time difference. Preferably, by considering the time requiring the time in which action of the agent of the present invention is exerted, an anticancer drug is administered predetermined time after the agent of the present invention is administered. Herein, the predetermined time is, for example, one to 72 hours (specific example, 48 hours). As in this case, the agent of the present invention is administered first, the action of the present invention is easily exerted. Thus, excellent clinical outcomes of therapy can be obtained.

Note here that a combination drug, in which the agent of the present invention and an anticancer drug are mixed, is prepared, and it may be administered to a subject.

When the agent of the present invention and an anticancer drug are used in combination, expression of a RFP gene or action of RFP is suppressed in target cancer cells. Thus, suppression of expression of TBP-2 by HDAC1 is suppressed or cancelled. As a result, the oxidative stress sensitivity of the target cancer cells is increased. In this way, a state in which the anticancer drug works effectively, that is, a state in which resistance to the anticancer drug is reduced is formed. Thus, the therapeutic effect by an anticancer drug can be improved.

The agent of the present invention is expected to be applied to various cancers. Cancers that is to be a target of the agent of the present invention include, esophageal cancer, oral cavity cancer, maxillary cancer, laryngeal cancer, pharyngeal cancer, gastric cancer, duodenal cancer, colon cancer, liver cell carcinoma, cholangiocellular carcinoma, lung cancer, prostate cancer, renal cancer, bladder papilloma, prostate cancer, urethral epidermoid cancer, osteosarcoma, chondrosarcoma, synovial sarcoma, myxosarcoma, liposarcoma, multiple myeloma, malignant lymphoma, squamous cell carcinoma, malignant melanoma (melanoma), glial tumor, meningioma, neuroblastoma, breast cancer, mammary sarcoma, carcinoma in situ of uterine, carcinoma in situ of uterine cervix, uterine adenocarcinoma, uterine sarcoma, ovarian carcinoma, malignant melanoma (melanoma), thyroid papillary carcinoma, follicular carcinoma of thyroid, acute myeloid leukemia, acute promyelocytic leukemia, acute myelomonocytic leukemia, acute monocytic leukemia, acute lymphatic leukaemia, acute undifferentiated leukemia, chronic myeloid leukemia, chronic lymphoid leukemia, and adult T-cell leukemia.

The anticancer drug to be used in combination is not particularly limited as long as it has the oxidative stress-inducing ability. Examples of the anticancer drug include platinum formulation such as cisplatin, carboplatin, and oxaliplatin, cyclophosphamide, fluorouracil (5-FU), etoposide, doxorubicin, bleomycin, and mitomycin. Two or more kinds of anticancer drugs can be used in combination. The dosage amount of the anticancer drug follows the use amount when it is used alone (that is, a usual use amount). However, since the action of an anticancer drug is expected to be enhanced by the combined use of the agent of the present invention, the dosage amount may be set to lower than the usual dosage amount. Note here that a person skilled in the art can set the "usual use amount" by taking a symptom, age, a sex, a body weight, and the like, of a patient into consideration.

(Method for Testing Anticancer Drug Resistance)

As a result of investigation by the present inventors, it has been revealed that high expression of RFP correlates to the reduction of expression of TBP-2 in a human colon carcinoma, and poor prognosis in a patient with colon carcinoma (see the below-mentioned Examples). Based on the findings, a second aspect of the present invention is to provide a method for testing the resistance to an anticancer drug using the expression amount of a RFP gene (hereinafter, referred to as "the testing method of the present invention"). The testing method of the present invention allows determining the resistance of cancer cells to an anticancer drug. The determination results can be used for determining, for example, treatment policies (selection of an effective treatment method, and the like). The use of the determination results improves clinical outcomes of therapy, makes prognosis better, improves quality of life (QOL) of patients, and the like. Thus, the testing method of the present invention provides information extremely useful for cancer treatment.

The testing method of the present invention includes the following steps: a step of examining an expression amount of RFP in cancer cells separated from a living body (detection step); and a step of determining resistance of the cancer cells to an anticancer drug having an oxidative stress-inducing ability based on the results of the above-mentioned step (determination step).

In the detection step, firstly, cancer cells separated from a living body are prepared. The term "separated from a living body" refers to a state in which a part of the living tissue including cancer cells to be tested is extracted and thereby cancer cells to be tested are completely isolated from the living body as the origin of the cancer cells. As long as this condition is satisfied, cancer cells may be in a state in which they form tissue together with the surrounding cells (that is, in a state of a tissue piece) or may be in a state in which they are separated from the surrounding cells. In the former case, cells may be prepared in such a manner that, for example, biopsy histological diagnosis (biopsy) is carried out, and in the latter case, cells may be prepared in such a manner that, for example, cytological diagnosis is carried out.

Subsequently, the expression amount of RFP in the prepared cancer cells is examined. The expression amount of RFP is usually calculated based on the comparison with control (comparison control). As the control, it is possible to use various cancer cells whose expression amount of RFP has been preliminary determined, and normal cells collected together with the cancer cells to be tested when the cancer cells to be tested are collected from a living body. It is not necessary to strictly quantitate the expression amount of RFP, but the expression amount of RFP may be detected in such a degree that the resistance of the cancer cells to be tested to an anticancer drug can be evaluated through comparison with control. Note here that as usually, the case in which the expression of RFP is observed in the cancer cells to be tested is also defined as RFP positive (or positive to RFP), and the case in which the expression of RFP in the cancer cells to be tested is not observed is also defined as RFP negative (or negative to RFP). When the expression amount of RFP of the cancer cells to be tested is detected by immunohistochemistry (detail is described in later), for example, when staining of not less than 10% of the cancer cells to be tested is recognized (that is to say, the rate of the stained cells is not less than 10%), the cells are determined to be RFP positive (or positive to RFP). A boundary value for distinguishing positive from negative (which is represented by the rate of the stained cells) may be appropriately set according to the detection method or detection conditions. For example, a boundary value can be set to 5% to 30%.

The expression amount of RFP is detected by the protein level or the mRNA level. When high accuracy is required, the former is better. When the expression amount of RFP is detected by the protein level, that is to say, when the RFP protein amount is examined as the expression amount of RFP, a western blotting method or immunohistochemistry (immunostaining) may be used although the method is not limited thereto. By the immunohistochemistry, the form or distribution state of the cancer cells to be tested can be examined at the same time, additional information can be obtained at the same time.

In the immunohistochemistry, an antibody specifically recognizing RFP (anti-RFP antibody) is used, and the amount of RFP protein is examined using a binding property (a binding amount) of the antibody as an indicator. The immunohistochemistry using an anti-RFP antibody can be carried out by, for example, an ABC (Avidin-Biotin Complex) method, a PAP (Peroxydase-anti-Peroxydase Complex) method, a LAB (Linked Avidin-Biotin) method, a LSAB (Linked Streptavidin-Biotin) method, and the like. Standard protocol of each method is well known (see, for example, "Enzyme-labeled Antibody Method" 3rd revised edition, K. Watanabe and K. Nakane (ed), Gakusai Kikaku).

Types and origins of the anti-RFP antibodies to be used in the immunohistochemistry are not particularly limited. Preferably, a monoclonal antibody is used, but an oligoclonal antibody (a mixture of several types to several tens types of antibodies) or a polyclonal antibody can be used as long as RFP can be detected with sufficient specificity. Antibody fragments such as Fab, Fab', $F(ab')_2$, scFv, and dsFv antibodies can be used. The anti-RFP antibody can be prepared by immunologic procedure, a phage display technique, a ribosome display method, and the like. Note here that the document "Shimono, Y. et al. RET finger protein is a transcriptional repressor and interacts with enhancer of polycomb that has dual transcriptional functions. J Biol Chem. 275(50): 39411-9 (2000)" describes a preparation method of an anti-RFP antibody (rabbit polyclonal antibody) and use thereof, and it can be referred to.

Hereinafter, an example of the methods and procedures of immunohistochemistry is shown.

(1) Immobilization—Paraffin Embedding Method

Tissue collected from a living body (in necropsy, a dead body) is immobilized in formalin, paraformaldehyde, and the like, and then embedded in paraffin. In general, it is dehydrated with alcohol, treated with xylene, and finally embedded in paraffin. The paraffin embedded specimen is cut into a desired thickness (for example, 3 to 5 µm) and extended on a slide glass. Instead of the paraffin embedded specimen, a frozen specimen may be used.

(2) Deparaffinization

In general, treatment is carried out with xylene, alcohol, and purified water sequentially in this order.

(3) Pretreatment (Antigen Activation)

If necessary, for antigen activation, for example, enzyme treatment, heat treatment and/or pressurization treatment are carried out.

(4) Removal of Endogeneous Peroxidase

When peroxidase is used as a labeling material for staining, endogeneous peroxidase activation is removed by carrying out treatment with hydrogen peroxide solution.

(5) Non-Specific Reaction Inhibition

Non-specific reaction is inhibited by treating a section with bovine serum albumin solution (for example, 1% solution) for several minutes to several tens minutes. Note here that this process may be omitted when the following primary antibody reaction is carried out by using an antibody solution containing bovine serum albumin.

(6) Primary Antibody Reaction

An antibody diluted to an appropriate concentration is dropped on the section on the slide glass and allowed to react for ten minutes to several hours. After reaction, the reacted product is washed with an appropriate buffer solution such as phosphate buffer.

(7) Addition of Labeling Reagent

As the labeling material, peroxidase is frequently used. A secondary antibody to which peroxidase is allowed to bind is dropped on the section on the slide glass and then allowed to react for ten minutes to several hours. After reaction, the reacted product is washed with an appropriate buffer solution such as phosphate buffer.

(8) Color Reaction

DAB (3,3'-diaminobenzidine) is dissolved in Tris buffer solution. Then, hydrogen peroxide solution is added. The thus prepared coloring solution is allowed to permeate into the section for several minutes (for example, five minutes) so as to color the section. After coloring, the section is sufficiently washed with tapped water so as to remove DAB.

(9) Nuclear Staining

The section is subjected to nuclear staining by reacting it with Mayer hematoxylin for several seconds to several tens seconds. It is washed with flowing water for saddening (in general, for several minutes).

(10) Dehydration, Clearing, Encapsulation

The section is dehydrated with alcohol, subjected to clearing treatment with xylene, and finally encapsulated with synthesized resin, glycerine, rubber syrup, and the like.

For detection and measurement of mRNA when the expression amount of RFP is examined on the mRNA level, RT-PCR (Molecular Cloning, Third Edition, 8.46, Cold Spring Harbor Laboratory Press, New York), a Northern blotting method (Molecular Cloning, Third Edition, 7.42, Cold Spring Harbor Laboratory Press, New York), a dot blotting method (Molecular Cloning, Third Edition, 7.46, Cold Spring Harbor Laboratory Press, New York), a method using a DNA chip (DNA array), in situ hybridization, and the like, can be used.

A person skilled in the art can design a nucleic acid primer or a nucleic acid probe suitable for each method by a conventional method based on the sequence of RFP (NCBI database, Accession: RFPNM_006510, DEFINITION: *Homo sapiens* tripartite motif-containing 27 (TRIM27), mRNA. (SEQ ID NO: 2)).

In the determination step, the resistance of cancer cells to an anticancer drug having the oxidative stress-inducing ability is determined based on the result of the detection step, that is to say, the expression amount of RFP. Hereinafter, specific examples of evaluation based on the expression amount of RFP is shown.

A plurality of evaluation divisions for relating between the expression amount of RFP and the anticancer drug resistance are previously set. Then, the evaluation division corresponding to the cancer cells to be tested is determined based on the expression amount of RFP obtained in the decision step. As specific examples of setting of the evaluation divisions, an example focusing on the presence or absence of expression of RFP (example 1) and an example focusing on the degree of expression of RFP (example 2) are shown below. Note here that division name: expression amount of RFP related to the division:evaluation results related to the division, are described in this order.

Example

Division 1: RFP positive: anticancer drug resistance
Division 2: RFP negative: anticancer drug sensitive Example Division 1: expression of RFP is not observed: anticancer drug sensitive
Division 2: weak expression of RFP is observed: low resistance to an anticancer drug
Division 3: moderate expression of RFP is observed: moderate resistance to an anticancer drug
Division 4: strong expression of RFP is observed: high resistance to an anticancer drug The number of evaluation divisions, and the expression amount of RFP and evaluation results related to each evaluation division are not necessarily limited to the above-mentioned examples, and they can be arbitrarily set through preliminary experiment, and the like. Note here that determination and evaluation in the present invention can be carried out automatically and mechanically without relying on the determination by persons skills in the art, for example, doctors and laboratory technicians.

As mentioned above, treatment policy can be determined by using the determination results of the testing method of the present invention. For example, when the determination result: "having anticancer drug resistance" or "having high resistance to an anticancer drug" is obtained, it is possible to predict that single use of an anticancer drug cannot exhibit a desired therapeutic effect. In such a case, an effective treatment policy is to use the agent of the present invention in combination with an anticancer drug so as to enhance action of the anticancer drug. On the other hand, the determination result: "anticancer drug sensitivity" or "anticancer drug resistance is low" is obtained, it is possible to predict that single use of an anticancer drug can exhibit the expected therapeutic effect. In such a case, one of the options of effective treatment policy is to use an anticancer drug singly. However, also in such a case, in order to improve the therapeutic effect by enhancing action of the anticancer drug, the action enhancing agent of the present invention may be administered in combination.

(Biomarker for Estimating Prognosis and Use Thereof)

As a result of the investigation by the present inventors, it has been revealed that high expression of RFP correlated to poor prognosis in patients with colon carcinoma or patients with endometrial cancer (see the below-mentioned Example). Based on the findings, a third aspect of the present invention is to provide a marker composed of RFP for estimating prognosis in cancer patients. The biomarker is useful for understanding the prognosis in cancer patients. Furthermore, it may be a guide for determining operative methods. For example, when the expression of RFP is observed in a specimen (cancer cells) collected from a patient with endometrial cancer (for example, immunostaining shows positive), it is possible to determine it is preferable that more aggressive operation is employed. More aggressive operation may include radical hysterectomy and lymphadenectomy.

This aspect provides the method for estimating prognosis in cancer patients is provided as the use of the above-mentioned biomarker. According to the method of estimating prognosis in accordance with the present invention, information about estimation of prognosis in cancer patients is obtained. For example, the information is used for determining treatment policy (selection of effective method of treatment, and the like). The use of the determination results improves clinical outcomes of therapy, makes prognosis better, improves quality of life (QOL) of patients, and the like.

The following is a detailed description of this aspect of the present invention in this aspect. Matters common in the first or second aspect employs the description in the first or second aspect. In the specification, the "biomarker for estimating prognosis in cancer patients" refers to a biomolecule that is an indicator for estimating prognosis in cancer patients. Types of "cancers" are not particularly limited. However, the biomarker of the present invention is particularly useful in estimation of prognosis in patients with colon carcinoma or endometrial cancer.

In the estimation method of prognosis in the present invention, the biomarker of the present invention is used as an indicator for determination. Specifically, prognosis in a cancer patient is estimated by using the expression amount of RFP in cancer cells separated from the cancer patient as an indicator. More specifically, a step of detecting the expression amount of RFP in cancer cells separated from the cancer patient (detection step) and a step of estimating prognosis based on the detection results (prognosis estimation step) are carried out. The detection step herein may be carried out similar to the detection step of the above-mentioned second aspect. Examples of cancer patients include patients with colon carcinoma or endometrial cancer.

In the prognosis estimation step, prognosis in a cancer patient is estimated by using the expression amount of RFP in cancer cells as an indicator. Basically, determination criterion is employed, in which prognosis is determined to be poor when the expression amount of RFP is large. Hereinafter, specific examples of evaluation based on the expression amount of RFP are described.

A plurality of evaluation divisions for relating between the expression amount of RFP and prognosis are previously set. Then, the evaluation division corresponding to the cancer cells is determined based on the expression amount of RFP obtained in the decision step. As specific examples of setting of the evaluation divisions, an example focusing on the presence or absence of expression of RFP (example 1) and an example focusing on the degree of expression of RFP (example 2) are shown below. Note here that division name: expression amount of RFP related to the division:evaluation results related to the division, are described in this order.

Example

Division 1: RFP positive: prognosis is poor
Division 2: RFP negative: prognosis is good Example Division 1: expression of RFP is not observed: prognosis is good
Division 2: weak expression of RFP is observed: prognosis is relatively good
Division 3: moderate expression of RFP is observed: prognosis is relatively poor
Division 4: strong expression of RFP is observed: prognosis is poor The number of evaluation divisions, and the expression amount of RFP and evaluation results related to each evaluation division are not necessarily limited to the above-mentioned examples, and they can be arbitrarily set through preliminary experiment, and the like. Note here that determination and evaluation in the present invention can be carried out automatically and mechanically without relying on the determination by persons skills in the art, for example, doctors and laboratory technicians.

The present invention further provides a reagent for estimating prognosis in cancer patients and a kit for estimating prognosis in cancer patients. The reagent of the present invention is composed of an anti-RFP antibody. The types and origin of the anti-RFP antibodies employ the corresponding description in the second aspect. When labeled antibody is used as the anti-RFP antibody, the amount of bonded antibody can be directly detected by using a labeled amount as an indicator. Therefore, a simpler testing method can be constructed. On the contrary, this method poses problems that an anti-RFP antibody to which a labeling agent binds and in addition, detection sensitivity is generally lower. Then, it is preferable that indirect detection methods such as a method using a secondary antibody to which a labeling agent binds, and a method using a polymer, to which a secondary antibody and a labeling agent bind, are used. The secondary antibody herein denotes an antibody having specific connectivity with respect to an anti-RFP antibody. For example, when an anti-RFP antibody is prepared as a rabbit antibody, an anti-rabbit IgG antibody can be used. Labeled secondary antibodies usable for various antibodies such as rabbit, goat, and mouse are commercially available (for example, Funakoshi Co., Ltd., Cosmo Bio Co., Ltd., or the like), and the antibodies can be appropriately selected according to reagents of the present invention.

Examples of the labeling agent include enzymes such as peroxidase, microperoxidase, horseradish peroxidase (HRP), alkaline phosphatase, β-D-galactosidase, glucose oxidase, and glucose-6-phosphate dehydrogenase; a fluorescent substance such as fluorescein isothiocyanate (FITC), tetramethylrhodamine isothiocyanate (TRITC), and europium; chemoluminescence substance such as luminal, isoluminol, and acridinium derivative; coenzyme such as NAD; biotin; as well as radioactive substances such as $^{131}$I and $^{125}$I.

In one embodiment, the reagent of the present invention is formed in a solid phase in accordance with its use. Insoluble support media used for making solid phase is not particularly limited. For example, insoluble support media made of water-insoluble materials, for example, resin such as a polystyrene resin, a polycarbonate resin, a silicon resin, and a nylon resin, and glass can be used. Antibodies can be supported by the insoluble support media by physical adsorption or chemical adsorption.

A kit of the present invention includes the reagent of the present invention as a main component element. The kit may include other reagents (buffer solution, blocking reagent, enzyme substrate, color reagent, and the like) and/or devices or instruments (vessel, reaction device, fluorescence reader, and the like) to be used for carrying out the testing method. Furthermore, it is preferable that a kit includes RFP as a standard reagent. Note here that in general, a kit of the present invention includes an instruction manual.

EXAMPLES

Based on the hypothesis that HDACi regulates the antioxidation mechanism in cells so as to allow cancer cells to be sensitive to an anticancer drug, the below-mentioned experiments are carried out.

1. Materials and Methods
(1) Plasmids

The pcDNA3-HDAC1-Flag was generously provided by Dr. Kawaguchi (Aichi prefectural colony, Japan). The full-length NF-YA, NF-YB, NF-YC, HDAC1, HDAC1 deletion fragments and TBP-2 cDNA were cloned into the pcDNA3.1/V5-His-TOPO vector according to the manufacturer's instructions. The HDAC1 cDNA from pcDNA3.1/V5-His-HDAC1 was inserted into the pcDNA3.1/myc-His vector. The pFlag-RFP construct was described previously (reference 20). The RFP cDNA was inserted into the pEGFP-C1 vector.

(2) RNAi

HDAC1 siRNA was purchased from Dhamacon. RFP, TBP-2, NF-YC and control siRNAs were purchased from QIAGEN. The siRNAs were transfected using Lipofectoamine 2000 (Invitrogen) according to the manufacturer's instructions. For shRNA-mediated knockdown of RFP, a set of single-stranded oligonucleotides encoding the RFP target or negative control shRNA and their complement were synthesized as follows (only the sense sequences were shown) RNAi
shRFP:

(SEQ ID NO: 10)
5'-GATCGAGTTACTCGGGAGGGAAATTCAAGAGATTTCCCTCCCGA

GTAACTCTTTTTTGGAAA-3'

The complementary oligonucleotide pair is inserted into a pSilencer3.1-H1 neo vector (Ambion), which is used as a shRNA expression vector.

(3) Generation of Cell Lines Stably Expressing shRNA

HeLa cells were transfected with the shRNA expression vector with Lipofectoamine 2000. Transfected cells were then selected by neomycin for 2 weeks.

(4) Cell Viability Assay $8 \times 10^3$ cells were seeded in each well of 96-well plates and 24 h later were treated with $H_2O_2$ (10 h) or cisplatins (24 h) at the concentration as described. Cell viability was measured by WST-1 assay (Roche). In the graph, the index of non-treatment group was defined as 1

(5) RT-PCR

Total RNA from HeLa cells transfected with siRNA was isolated using the RNeasy Mini Kit (Qiagen). cDNA transcripts were then generated using Superscript II (Invitrogen). RT-PCR was performed with primers specific to HDAC1 (sense; 5'-CTCCTGTTTTTTTCAGGCTCC-3' (SEQ ID NO: 11), anti-sense; 5'-AGGAGAAGACAGACA-GAGGGC-3' (SEQ ID NO: 12)), RFP (sense; 5'-TGCTC-GACTGCGGCCATAAC-3' (SEQ ID NO: 13), anti-sense; 5'-TCGGTGCGCAGCTGCTTTAC-3' (SEQ ID NO: 14)), TBP-2 (sense; 5'-TGAGATGGTGATCATGAGACC-3' (SEQ ID NO: 15), anti-sense; 5'-GTATTGACATCCACCA-GATCC-3' (SEQ ID NO: 16)), GAPDH (sense; 5'-GAAG-GTGAAGGTCGGAGTCAA-3' (SEQ ID NO: 17), anti-sense; 5'-GAGATGATGACCCTTTTGGCTC-3' (SEQ ID NO: 18)).

(6) Immunoprecipitation and Western Blotting

Cells were washed twice with ice-cold PBS and lysed in lysis buffer (50 mM Tris-HCl, pH 7.4, 120 mM NaCl, 5 mM $MgCl_2$, 0.8% Nonidet P-40, 10% glycerol, 1 mM DTT and 1 mM PMSF) containing Complete protease inhibitor mixture. The lysates were briefly sonicated and immunoprecipitated with the indicated antibodies. Purified normal rabbit or anti-HA tag antibody were used as a control. Electrophoretic separation, and Western blotting were performed as previously described (Reference 20). For western blotting with immunoprecipitates by using rabbit polyclonal antibody, we used Relia Blot (Bethyl Laboratories) according to the manufacturer's instructions.

(7) Chromatin Imunoprecipitation (ChIP) Assay

ChIP experiments were carried out as previously described (Reference 28). Briefly, formaldehyde-crosslinked chromatin from indicated cells was sonicated, and the resulting chromatin fragments were immunoprecipitated with anti-HDAC1, anti-acetylated H3, anti-acetylated H4, anti-RFP, or anti-NFYB antibodies. Purified normal rabbit or mouse IgG were used as a control. Formaldehyde crosslinks were reversed by adding 5 M NaCl for a final concentration of 0.2M and incubated for 8 h at 65° C. Purified DNA and input DNA were amplified by PCR at 32-37 cycles.

(8) In vivo Treatment Model

Contorol or HeLa cells stably expressing shRNA were subcutaneously injected into the back region of female nude mice (7 weeks). When the mean tumor volume reached at least 50 mm$^3$, animals were randomly assigned to control and treatment groups before the first treatment of cisplatin. One mg/kg of Cisplatin or Vehicle (saline: control) was intraperitoneally administered every 4 day. The volume of a tumor is calculated from the following equation after the tumor diameter is measured by using calipers.

Volume=(Major axis×Minor axis×Minor axis)/2

(9) Immunohistochemistry

Formalin-fixed, paraffin-embedded sections from colon carcinoma patients were deparaffinized and rehydrated. Slides were rinsed thoroughly with Protein Blocking Agent (UltraTech HRP Streptavidin-Biotin Detection System, Beckman Coulter) and endogenous peroxidase was blocked in 3% hydrogen peroxide. Antigen retrieval was done by autoclaving at 121° C. for 10 min in 0.1 mol/L citrate buffer (pH 7.0) with 0.5% NP-40 (Sigma-Aldrich). The sections were incubated with rabbit polyclonal anti-RFP antibody and then, the secondary biotinylated goat polyvalent antibody (Beckman Coulter) was applied. The samples were incubated with peroxidase-conjugated streptavidin and the reaction products were visualized using 3,3'-diaminobenzidine tetrahydrochloride (DAB). When >10% of the tumor cells were stained with the antibody, it was categorized as positive for antigen expression.

Kaplan-Meier plots were used to estimate the prognostic relevance of RFP in univariate analysis using Stat view.

(10) Immunofluorescence

Formalin-fixed, paraffin-embedded sections from colon carcinoma patients were deparaffinized and dehydrated. Antigen retrieval was done by microwave heating for 10 min in citrate buffer (pH 6). Samples were blocked by 1% BSA in PBS and incubated with anti-RFP polyclonal antibody and anti-TBP-2 monoclonal antibody. Then samples were stained with Alexa Fluor 594-conjugated anti-rabbit IgG antibody, Alexa Fluor 488-conjugated anti-mouse IgG antibody and DAPI. Slides were mounted and observed using a confocal microscope.

(11) Patients with Endometrial Cancer

Test samples (119 specimens) collected from patients with endometrial endometrioid adenocarcinoma who underwent surgical treatment at Nagoya University Hospital between 1992 and 2007 were used for experiments under informed consent. Ages of patients ranges from 28 to 86 (median age: 57). None of these patients had undergone neoadjuvant chemotherapy. All patients underwent a total abdominal or radical hysterectomy plus bilateral salpingo-oophorectomy. Furthermore, 72 patients had lymphadenectomy. All patients were staged according to 1998 FigO (International Federation of Gynecology and Obstetrics) criteria. The 72 patients were stage I, 16 patients were stage II, 24 patients were stage III, and 7 patients were stage IV. Histological grade was assigned according to the World Health Organization classification. Fifty patients were G1, 51 patients were G2, and 18 patients were G3.

2. Results and Discussion

We first tested whether HDACi affect cellular sensitivity to the oxidative stress, using the HeLa human cervical cancer cell line. Treatment with Trichostatin A (TSA), a conventional HDACi, sensitized the HeLa cells to $H_2O_2$, a potent oxidative stress inducer (FIG. 1a). To investigate the molecular mechanism underlying this sensitization of cancer cells to oxidative stress, we focused on roles of HDAC1, which is a well studied member of HDACs. Knockdown of HDAC1 greatly increased cytotoxicity of $H_2O_2$ as well as cisplatin in HeLa cells (FIG. 1b-d). Although it is proposed that p53 associates with HDAC1 to regulate cellular sensitivity to the oxidative stress (References 16-19), other mechanisms may exist in HeLa cells in which p53 is inactivated by the papillomavirus protein E6.

Figure 2:
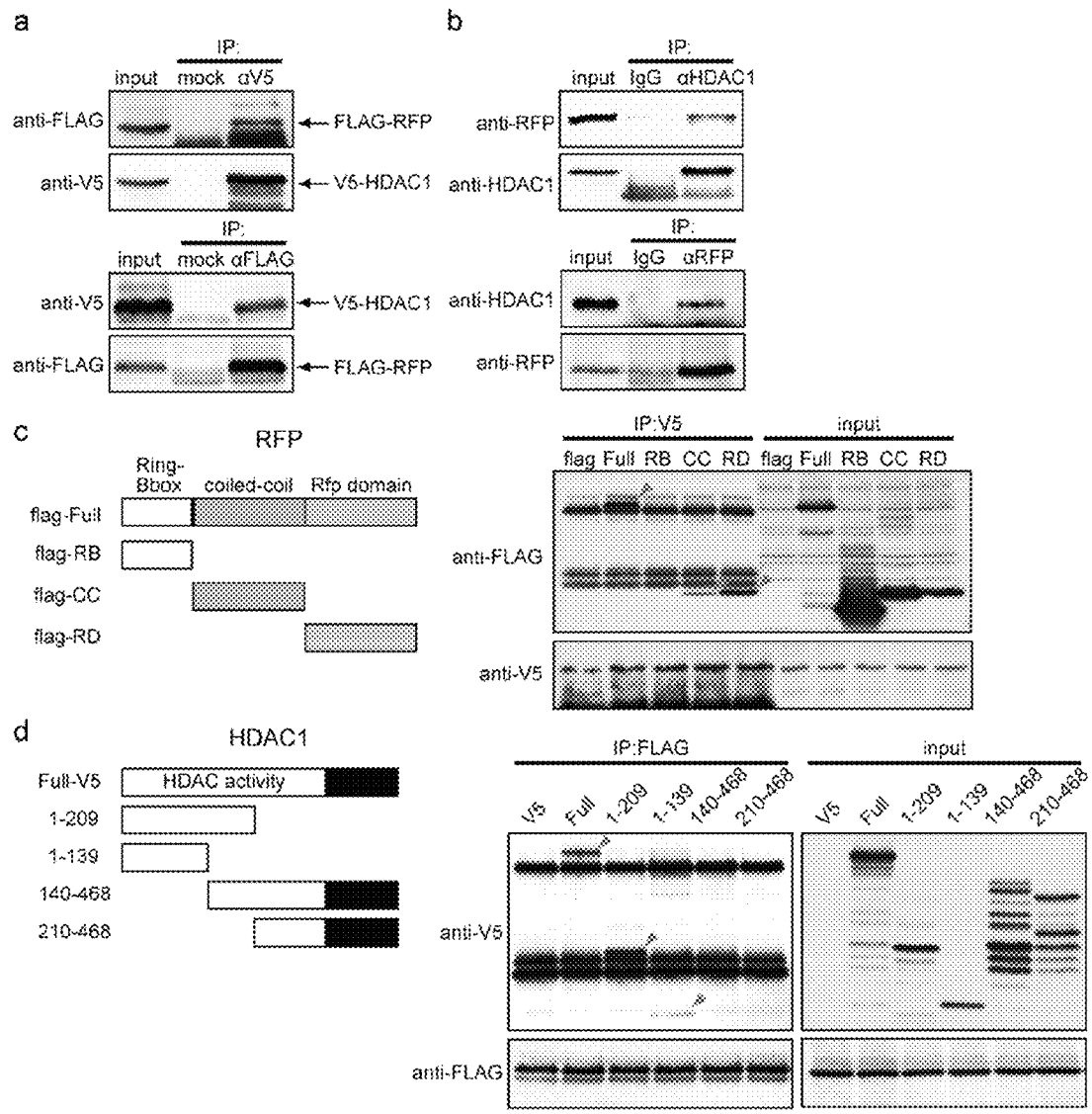
[FIG. 2] Identification of binding domains between HDAC1 and RFP. (a) HDAC1 interacts with RFP. HEK293 cells were transiently co-transfected with HDAC1-V5 and Flag-RFP. Cell lysates were immunprecipitated with anti-V5 (top panel) or anti-Flag (bottom panel) antibodies and the immunoprecipitates were analysed by western blotting with the indicated antibodies. Anti-HA antibody was used as mock. (b) Endogenous HDAC1 and RFP were immunoprecipitated with anti-HDAC1 (top panel) and anti-RFP (bottom panel) antibodies, respectively. The immunoprecipitates were analysed by western blotting with anti-HDAC 1 and anti-RFP antibodies. (c) The domain of RFP required for the association between HDAC1 and RFP. Left panel; Schematic illustration of RFP constructs. Ring finger, B-box zinc finger, Coiled-coil, and Rfp domain are indicated. The cDNA fragments corresponding to the indicated domains of RFP were tagged with Flag. Right panel; HEK293 cells were transiently co-transfected with HDAC1-V5 and Flag-tagged RFP deletion constructs, and immunoprecipitated with anti-V5 antibody, followed by immunoblotting with anti-Flag or anti-V5 antibody. The pFlag vector was used as control. (d) The region of HDAC1 required for the association between HDAC1 and RFP. Left panel; Schematic illustration of HDAC1 constructs. The cDNA fragments corresponding to the indicated regions of HDAC1 were tagged with V5. HEK293 cells were transiently co-transfected with Flag-RFP and V5-tagged HDAC1 deletion constructs and immunoprecipitated with anti-Flag, followed by immunoblotting with anti-V5 or anti-Flag antibody. Arrowheads indicate co-immunoprecipitated fragments. The pcDNA vector was used as control.

Since we previously found that RET finger protein (RFP), that is highly expressed in most of cancer cell lines, is associated and colocalized with HDAC1 (Reference 20), we tried to elucidated whether RFP is involved in the biological function of HDAC1 regarding the sensitivity to the oxidative stress. First we determined the binding domain of RFP and HDAC1. The amino-terminal region of HDAC1 bound to both coiled-coil and Rfp domain of RFP (FIG. 2). In addition, knockdown of either RFP or HDAC1 enhanced sensitivity of cancer cells to $H_2O_2$ and cisplatin (FIG. 1b-g), suggesting the possibility that HDAC1 is functionally associated with RFP.

Figure 3:
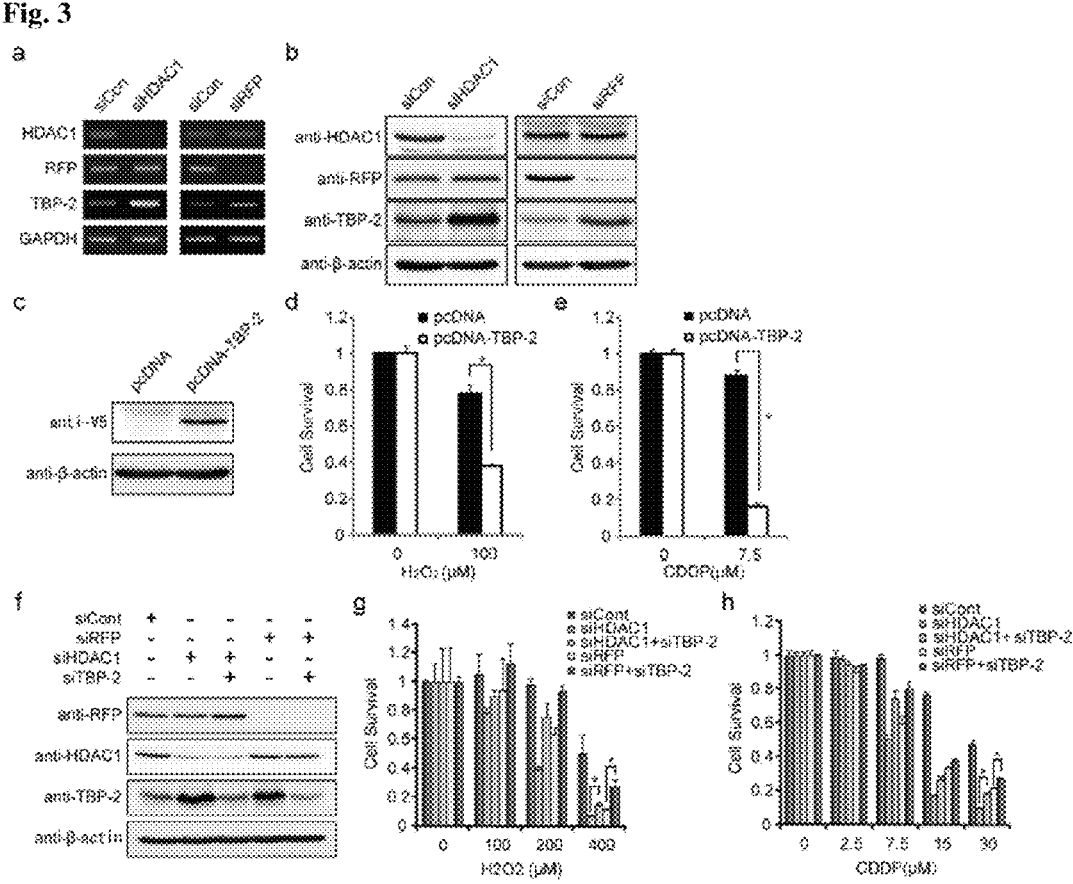
[FIG. 3] TBP-2 is a common target of HDAC1 and RFP, and responsible for sensitization of cancer cells to $H_2O_2$ and cisplatin. (a), (b) Knockdown of HDAC1 or RFP causes upregulation of TBP-2 expression. HeLa cells were transfected with control, HDAC1 or RFP siRNAs. Expression levels of HDAC1, RFP, or TBP-2 in these cells were analysed by RT-PCR in a and western blotting in b. In both RT-PCR and western blotting, expression of TBP-2 was observed to be increased by knockdown of HDAC1 or RFP. (c) Overexpression of TBP-2 in HeLa cells. HeLa cells were transfected with TBP-2-V5 and expression of V5-TBP-2 was detected by western blotting. (d), (e) Effect of TBP-2 overexpression on cellular sensitivity to $H_2O_2$ and cisplatin. HeLa cells transfected with TBP-2-V5 and treated for 10 h with $H_2O_2$ in d or for 24 h with cisplatin in e. Cell viability was measured by WST-1 assay and cell survival index of non-treatment group was defined as 1. Relative values with respect to 1, the cell survival index when treatment with $H_2O_2$ or cisplatin was not carried out, is shown. In cells with overexpression of TBP-2, the decreasing degree in the cell survival index is larger in the treated cells than in the control. (f) HeLa cells were transfected with control, HDAC1, RFP, or TBP-2 siRNAs. Total cell lysates were analysed by western blotting. It is shown that expression of TBP-2 that had been increased by knockdown of HDAC1 or RFP was suppressed by siTBP-2. (g), (h) HeLa cells were transfected as described in f. Cells were treated for 10 h with $H_2O_2$ (g) or for 24 h with cisplatin (h). Cell viability was measured and calculated as described in d, e. The cell survival index at the time when drugs are administered, which has been decreased by the knockdown of HDAC1 or RFP, is partially dissolved by the knockdown of TBP-2.

Because both HDAC1 and RFP have transcriptional repressor activity[1, 20, 21], we hypothesized that HDAC1 and RFP may cooperatively repress the common target genes which are responsible for the sensitization of cells to the cytotoxic agents. To identify such target genes, we generated stable HeLa cells expressing control or RFP short hairpin RNA (shRNA) and compared the gene expression profiles by DNA microarray. Among genes up-regulated in RFP-knockdown cells, we focused on the TBP-2 gene because it has also been reported to be significantly up-regulated by a HDAC inhibitor, SAHA (Reference 15). It is well known that TBP-2 inhibits thioredoxin (References 22 and 23), a scavenger of ROS, and sensitizes cells to oxidative stress and cisplatin (References 4 and 24). From the results of reverse transcription-polymerase chain reaction (RT-PCR) and western blot analysis, we confirmed that TBP-2 expression is transcriptionally regulated by HDAC1 and RFP (FIG. 3a, b). To test whether TBP-2 indeed sensitizes the cells to $H_2O_2$ and cisplatin, TBP-2 was overexpressed in HeLa cells. Overexpression of TBP-2 markedly increased the sensitivity to these agents (FIG. 3d, e), suggesting that the induced expression of TBP-2 in HeLa cells is responsible for the increased sensitivity to $H_2O_2$ and cisplatin in HDAC1 or RFP knockdown cells. We further examined whether the induced TBP-2 expression by siHDAC1 or siRFP account for the increased sensitivity. Knockdown of TBP-2 significantly recovered the cellular resistance to $H_2O_2$ and cisplatin, which was decreased by knockdown of HDAC1 or RFP (FIG. 3f-h). These results showed that HDAC1 and RFP increase cellular resistance to these agents in part by repressing the TBP-2 expression.

Figure 4:
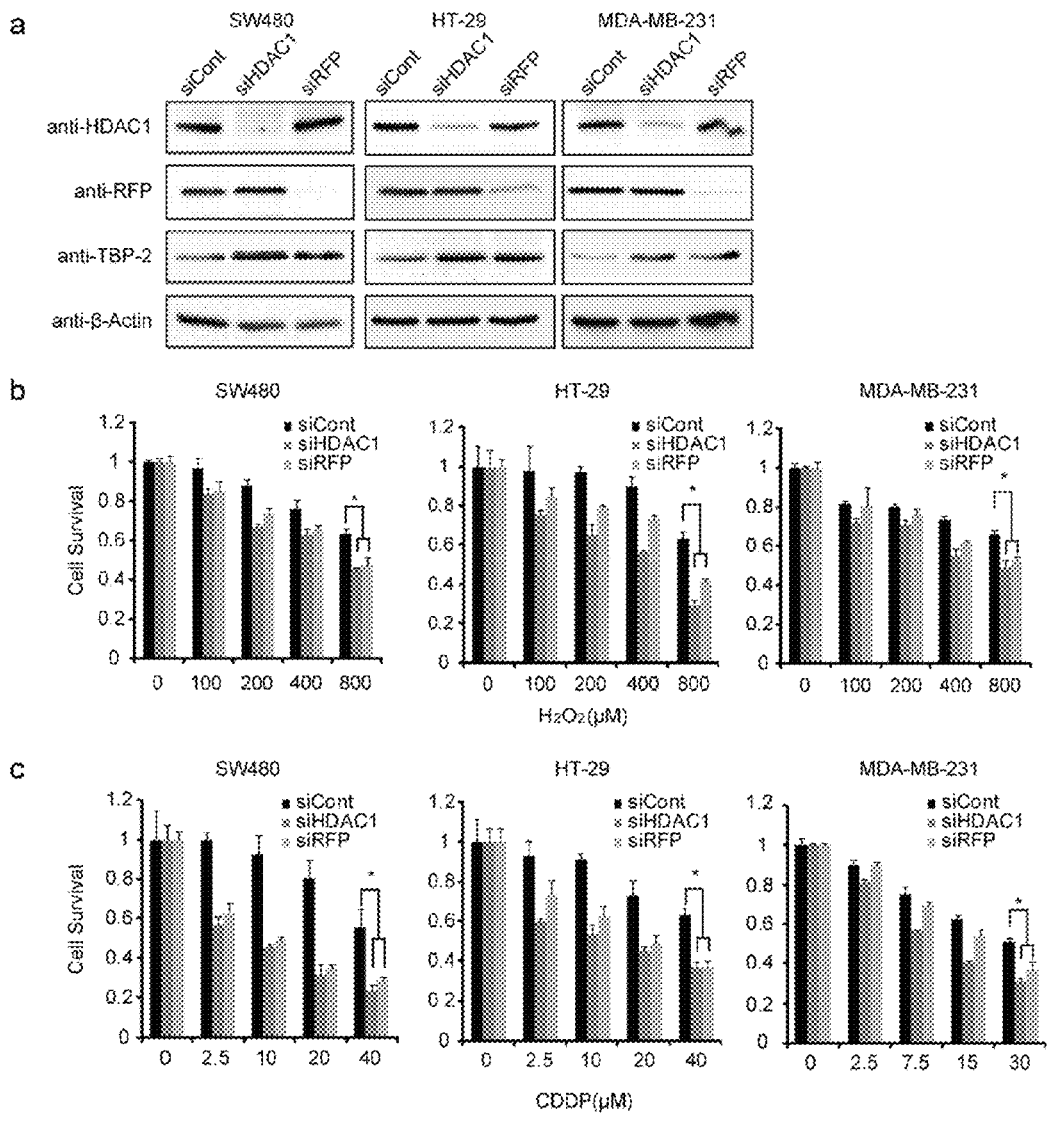
[FIG. 4] HDAC1 and RFP regulate TBP-2 expression and affect cellular sensitivity to $H_2O_2$ and cisplatin in colon and breast cancercell lines. (a) Colon (SW480, HT-29) and breast (MDA-MB-231) cancer cells were transfected with control, HDAC1, or RFP siRNA. Total cell lysates were subjected to western blotting. It was shown that when HDAC1 or RFP was knocked down in each cell line, expression of TBP-2 was increased. (b), (c) Cells were transfected with control, HDAC1, or RFP siRNA and treated for 10 h with $H_2O_2$ in b or for 24 h with cisplatin in c. Cell viability was measured by WST-1 assay and cell survival index of non-treatment group was defined as 1. In the knockdown cells of HDAC1 or RFP, the decreasing degree of the cell survival index is larger in the treated cells than in the control.

Furthermore, it was confirmed that the same results were observed when the cell lines of colon carcinoma and breast cancers were used (FIG. 4).

We performed chromatin immunoprecipitation (ChIP) to examine whether HDAC1 and RFP were recruited to the promoter region of the TBP-2 gene and directly regulate its expression. Both HDAC1 and RFP were recruited to the proximal, but not distal, region of the TBP-2 promoter. Luciferase reporter assay showed that HDAC1 and RFP can coordinately repress the TBP-2 promoter activity, and transcriptional repression activity of RFP was inhibited by HDACi (data now shown). Since the expression of TBP-2 is increased by the knockdown of RFP, it is thought that acetylation of histone in a TBP-2 promoter region is accelerated. ChIP using RFP kockdown cells showed an increase of the acetylation levels of the histone H3 and H4 at the promoter (FIG. 5b). Furthermore, recruitment of HDAC1 in a TBP-2 promoter region is weakened by the suppression of expression of RFP, the acetylation of histone by RFP knockdown is thought to be caused because HDAC1 is not recruited. These results strongly suggest that RFP recruits HDAC1 to the TBP-2 promoter region and represses its transcription thorough the HDAC activity.

Because neither HDAC1 nor RFP has been reported to directly bind to DNA, HDAC1-RFP complex might be recruited to the promoter by DNA binding proteins. Previous studies indicated that the proximal region of TBP-2 promoter includes NF-Y binding sequence and that the induction of TBP-2 expression by HDACi was regulated by NF-Y (Reference 15). Hence, we speculated that NF-Y may be a candidate that recruits the HDAC1-RFP complex to the TBP-2 promoter. NF-Y is a trimeric transcription factor consisted of NF-YA, B and C. Co-immunoprecipitation study revealed that RFP can specifically interact with NF-YC (FIG. 5c, d). This suggests that HDAC1, RFP, and NF-Y may form protein complex. To investigate this protein complex, NF-YC-V5, Flag-HDAC1 and Flag-RFP constructs were transiently co-transfected into HEK293 cells and was immunoprecipitated with anti-V5 antibody. HDAC1 and RFP were co-immunoprecipitated with NF-YC (FIG. 5e).

ChIP assay revealed that NF-Y is associated with the proximal region of TBP-2 promoter (FIG. 5f) as observed for HDAC1 and RFP, and knockdown of NF-YC markedly attenuated recruitment of both HDAC1 and RFP to the TBP-2 promoter (FIG. 5g, h). These results imply that HDAC1, RFP and NF-Y form protein complex on the TBP-2 promoter. In addition, from the results of gel filtration chromatography we found HDAC1, RFP and NF-YC were detected in the same fractions (around 400 kDa fractions). This fact supports that these proteins form a complex.

Figure 5:
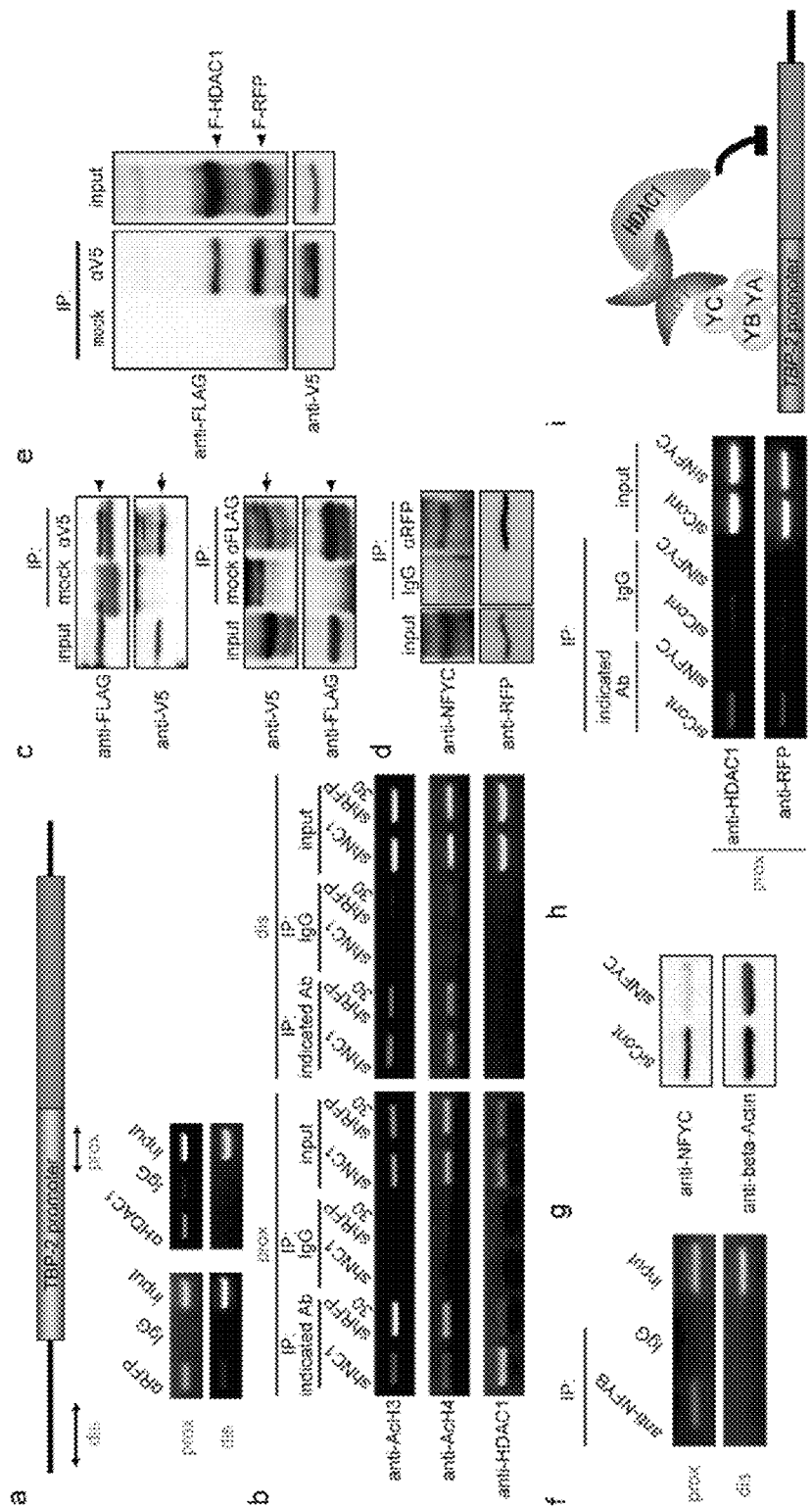
[FIG. 5] RFP recruits HDAC1 to TBP-2 promoter through the interaction with NF-YC. (a) The top panel shows schematic illustration of the TBP-2 promoter. Two regions used for ChIP analysis (proximal and distal) were indicated. The bottom panel shows that HDAC1 and RFP are recruited to the TBP-2 promoter. Crosslinked chromatin was immunoprecipitated using the indicated antibodies. PCR was used to detect two regions of the TBP-2 promoter with primers corresponding to the proximal and distal sequences. Input represents PCR amplification of the total input DNA. (b) RFP recruits HDAC1 to the TBP-2 promoter which deacetylates hisotne H3 and H4. Crosslinked chromatin from shNC1 and shRFP30 cells was immunoprecipitated using the indicated antibodies. PCR was carried out as described in a. (c) RFP interacts with NF-YC. HEK293 cells were transiently co-transfected with Flag-RFP and NF-YC-V5. Cell lysates were immunprecipitated with anti-V5 (top panel) or anti-Flag (bottom panel) antibodies and the immunoprecipitates were analysed by western blotting. Arrows indicate V5-NF-YC. Arrow heads indicate Flag-RFP. Anti-HA antibody was used as mock. (d) Endogenous RFP interacts with NF-YC. The immunoprecipitates of cells with anti-RFP or control IgG were analysed by western blotting with anti-RFP and anti-NF-YC antibodies. (e) Co-immunoprecipitation of HDAC1 and RFP with NF-YC. HEK293 cells were co-transfected with Flag-HDAC1, Flag-RFP, and NF-YC-V5 and immunoprecipitated with anti-V5 antibody. immunoprecipitates were subjected to western blot analysis. Anti-HA antibody was used as mock. (f) NF-Y binds to the proximal region of TBP-2 promoter. ChIP analysis was carried out with anti-NF-YB antibody. PCR was carried out as described in a. (g) siRNA-mediated knockdown of endogenous NF-YC in HeLa cells. Total cell lysates from HeLa cells transfected with NF-YC siRNA analysed by western blotting with NF-YC antibody. (h) NF-YC recruits HDAC1 and RFP to the TBP-2 promoter. Crosslinked chromatin from cells transfected with control or NF-YC siRNA was immunoprecipitated with anti-HDAC1 or anti-RFP antibodies. PCR was carried out as described in a. (i) Schematic illustration of the model for HDAC1/RFP/NF-YC complex formation on the TBP-2 promoter.
Figure 6:
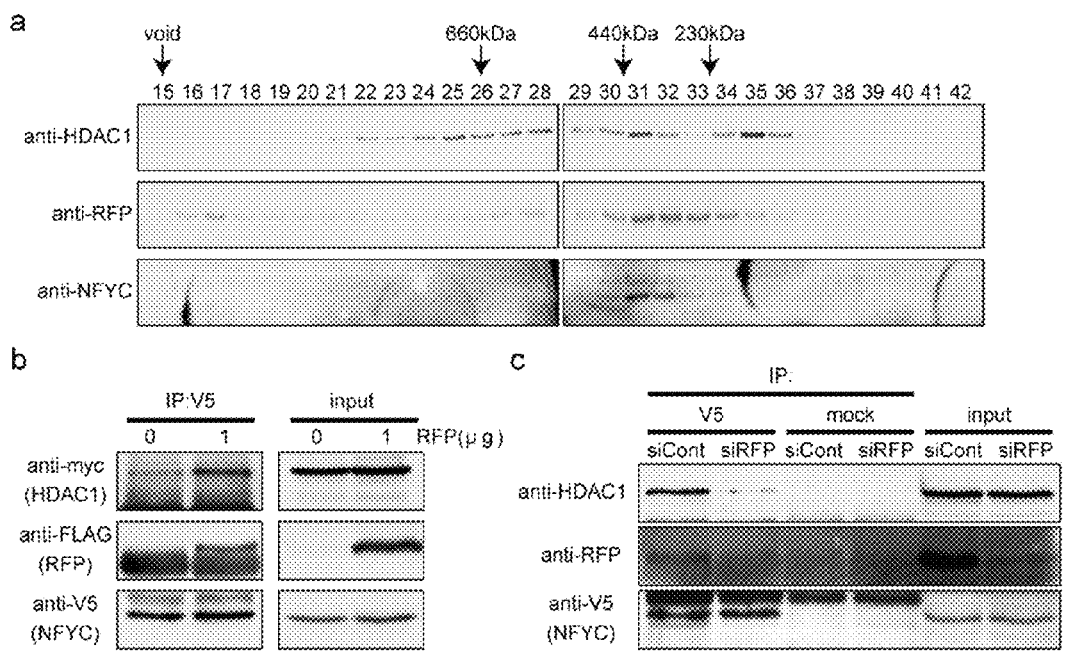
[FIG. 6] RFP mediates HDAC1/RFP/NF-YC complex formation. (a) HDAC1, RFP, and NF-YC are co-fractionated on gel filtration columns. HeLa cell extracts were separated by Superose 6 gel filtration chromatography and equal volumes of each fractions were run on SDS-PAGE gels. The fractions were then immunoblotted with anti-HDAC1, anti-RFP, and anti-NF-YC antibodies. The elution profile of molecular weight standards is given at the top (Void, blue dextran; 660 kDa, thyroglobulin; 440 kDa, ferritin; 230 kDa, catalase). (b) RFP expression enhances the complex formation. HEK293 cells were co-transfected with NF-YC-V5, HDAC1-myc, and Flag-RFP, and immunprecipitated with anti-V5 antibody. The immunoprecipitated samples were subjected to western blotting analysis with the indicated antibodies. (c) RFP depletion by RNAi disrupts the complex formation. NF-YC-V5 was co-transfected into HeLa cells with control or RFP siRNA. The cell lysates were immunoprecipitated with anti-V5 antibody, followed by western blotting with the indicated antibodies. Anti-HA antibody was used as mock.
Figure 7:
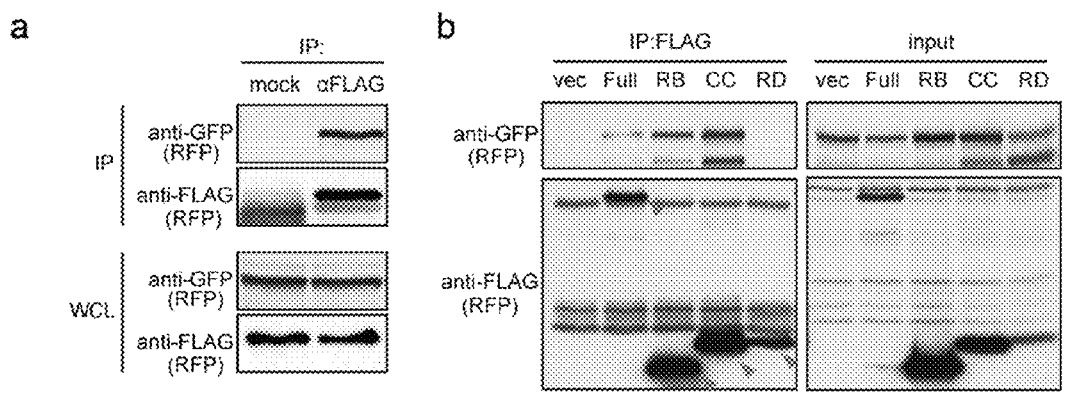
[FIG. 7] RFP Oligomerization (a) RFP forms homo-oligomer. HEK293 cells were co-transfected with GFP-RFP and Flag-RFP, and immunoprecipitated with anti-Flag antibody followed by immunoblotting with anti-Flag and anti-GFP antibodies. Anti-HA antibody was used as mock. WCL: whole cell lysates. (b) Ring-B-box and Coiled-coil domains, but not Rfp domain, of RFP were required for its oligomerization. HEK293 cells were co-transfected with GFP-RFP and Flag tagged RFP deletion constructs, and immunoprecipitated with anti-Flag antibody. The pFlag vector was used as control. Arrow heads indicate Flag-tagged RFP constructs.

The results shown in FIG. 5 suggested that RFP mediates the interaction between HDAC1 and NF-YC. Consistent with this view, the association between HDAC1 and NF-YC was enhanced in exogenously RFP-expressed cells, whereas it was conversely attenuated in RFP knockdown cells (FIG. 6b, c). These findings indicate that RFP mediate the formation of the protein complex. Since RFP has been reported to form oligomer (References 25 and 26), we determined the domain required for its oligomerization. As shown in FIG. 7b, Ring-B-box (RB) and Coiled-coil (CC) domain, but not Rfp domain (RD), of RFP is required for RFP-RFP oligomerization.

Since experiments so far showed that an Rfp domain was necessary for RFP to bind to HDAC1 and NF-YC, it was thought that RFP was polymerized in RB and CC at the N-terminal side, and it bound to HDAC1 and NF-YC respectively in an Rfp domain at C-terminal side so as to form a HDAC1-RFP-NF-Y protein complex (FIG. 5i).

Figure 8:
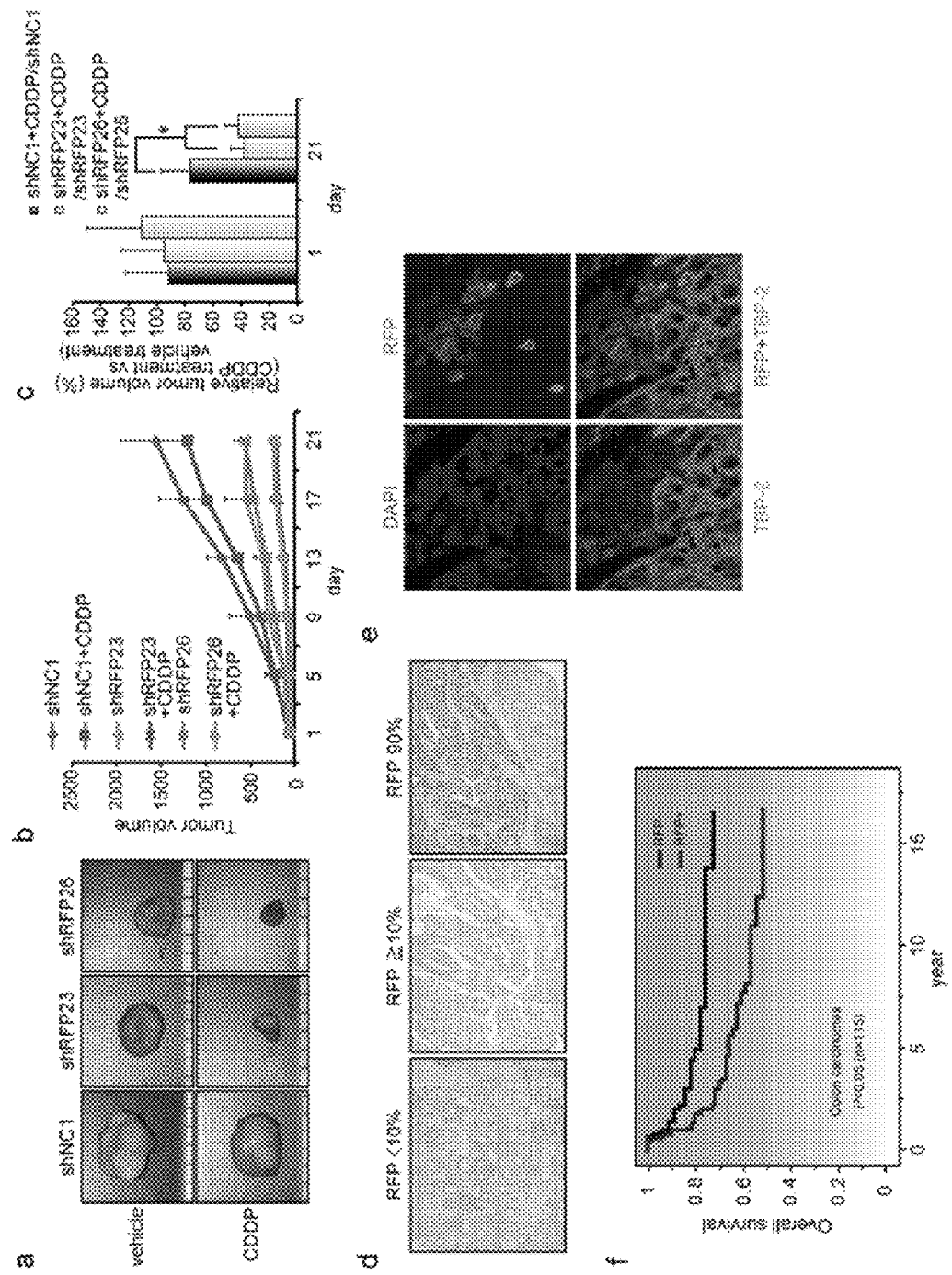
[FIG. 8] RFP is a novel target for cancer therapy. (a), (b), (c) Knockdown of RFP enhances the sensitivity of tumors to cisplatin in vivo. Mice were subcutaneously injected with shNC1, shRFP23 or shRFP26 cell lines. When the mean tumor volume reached at least 50 mm$^3$, animals were randomly assigned to control and treatment groups before the first treatment of cisplatin. 1 mg/kg of Cisplatin or Vehicle (saline) was intraperitoneally administered every 4 day. Photographs of representative tumours are shown in a. It is shown from visual observation that a tumor volume in the treatment group of the RFP knockdown cell line is remarkably smaller than that in the non-treatment group. Tumor growth curve was shown in b. The tumor growth is remarkably slower in the treatment group of the RFP knockdown cell line as compared with that in the non-treatment group. The mean tumor volume of non-treatment group (vehicle) was defined as 100% and compared with that of treatment group on day 1 and day 21 in c. In shNC1, the tumor volume was about 92% with respect to the non-treatment group on day 1 and it decreased to 77% on day 21. While in shRFP23 and shRFP26, the volumes were decreased from 95% to 38%, and from 112% to 42%, respectively. The therapeutic effect of cisplatin was significantly enhanced in the group using RFP knockdown cell line. (d) RFP expression in representative tumor tissues from colon carcinoma patients. Brown is indicative of staining with a RFP polyclonal antibody. When the stained cells are <10%, the cells are determined to be RFP-negative, and when the stained cells are ≧10%, the cells are determined to be RFP positive. (e) RFP represses the expression of TBP-2 in colon carcinoma patient. Tumor tissues were stained with anti-RFP polyclonal antibody (red) and anti-TBP-2 monoclonal antibody (green). Cell nuclei were labeled with DAPI (4',6-diamino-2-phenylindole). In the cells showing RFP expression, expression of TBP-2 is shown to be low. (f) RFP expression correlates with poor prognosis in colon carcinoma patients. Overall survival of 115 patients with colon carcinomas were stratified by RFP expression and analyzed by Kaplan-Meier plot. A log-rank test showed significant differences between RFP+ and RFP− groups.

Furthermore, the effect of the expression of RFP in, in vivo anticancer drug treatment models was studied. A cell line in which control (shNC1) and shRNA of RFP (shRFP23 and shRFP26) had been expressed were subcutaneously transplanted into a nude mouse. When tumors grew to larger than volume of 50 mm³, ciplatin was injected intraperitoneally every four day. Treatment with cisplatin more markedly suppressed tumor growth of RFP knockdown cells than control cells (FIG. 8a-c).

Lastly, we analysed the effect of RFP expression on the prognosis of cancer patient. We obtained specimens with 115 colon carcinoma patients. RFP-positive colon cancer was defined when more than 10% of tumor cells were clearly stained with anti-RFP antibody. As a result, 68 out of 115 colon carcinoma samples were RFP-positive (FIG. 8d). Expression of RFP and TBP-2 were exclusive and TBP-2 expression was clearly down regulated in RFP expressing cells in colon cancer specimen (FIG. 8e). Kaplan-Meier survival analysis of these cases revealed a significant correlation between RFP expression and shorter overall survival (FIG. 8f). These results suggest that the levels of RFP expression in colon cancer affect efficacy of anticancer drugs as well as clinical outcome of the patients.

The synergistic anti-tumor effects of HDACi and chemotherapeutic agents have received considerable attention in research for cancer treatment, however, the mechanistic basis of the synergy has not been fully clarified. Several studies have suggested the putative mechanism that HDAC1 regulates cellular sensitivity to apoptosis induced by various stresses through the association with p53 (References 16-19). We presented here direct evidence that HDAC1 form a complex with RFP and NF-YC and regulates the sensitivity of cancer cells to oxidative stress through the repression of TBP-2 expression. Based on previous reports, up-regulated TBP-2 expression may reduce the ROS scavenging ability of thioredoxin and sensitize cancer cells to oxidative stress induced by anti-cancer drugs. With the view of these data, HDAC1 confers the cancer cells resistance to anti-cancer agents by regulating the state of anti-oxidant system.

Moreover, we demonstrated that knockdown of RFP significantly sensitized cancer cells to anti-cancer drug. Thus, RFP could become a novel target for anticancer therapy in combination with other anti-cancer drugs. Although HDACi have potent anticancer activities at concentrations that are minimally toxic to the host, dose-limiting toxicities were also observed (Reference 28). Given the tissue-restricted expression of RFP in normal cells (Reference 29) and no apparent phenotypic defects in RFP knockout mice, the development of RFP-targeted cancer therapy may be beneficial with less toxicity.

Our finding could provide a new insight into the molecular mechanism that underlies the synergy between HDACi and anti-cancer drugs.

Figure 9:
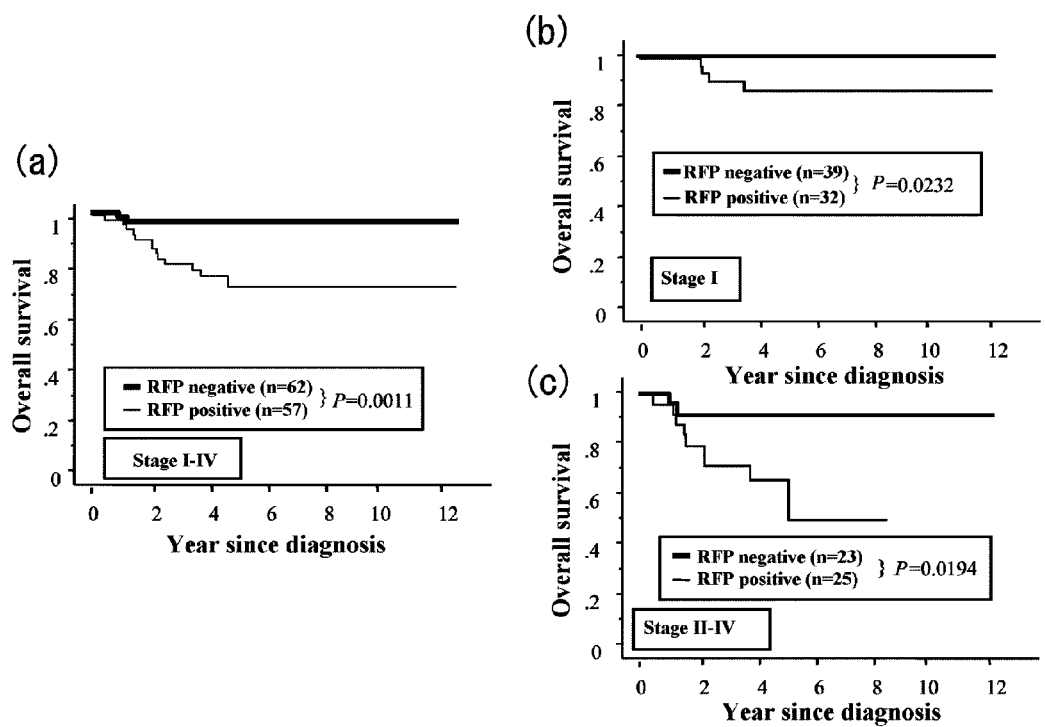
[FIG. 9] Graphs showing the correlation between RFP expression and poor prognosis in endometrial cancer. The RFP negative group and the RFP positive group were compared with each other in overall survival. (a) Comparison in all patients groups. (b) Comparison in the patients group of the stage I. (c) Comparison in the patients group of the stages II to IV.
Figure 10:
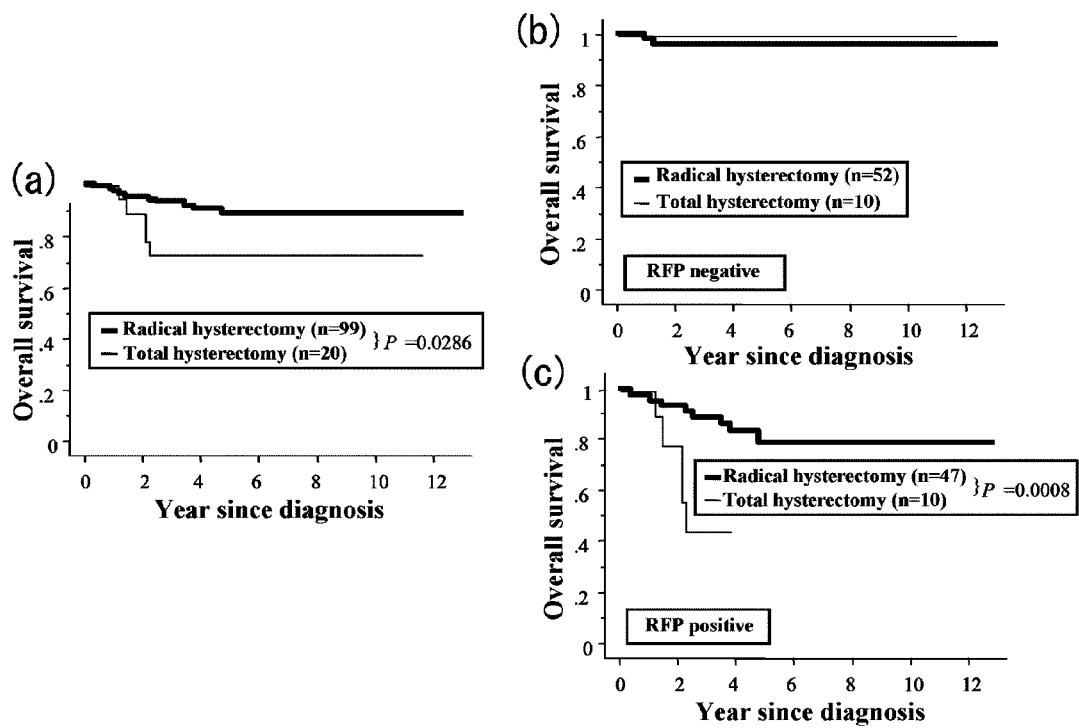
[FIG. 10] Graphs showing the RFP expression and the difference of prognoses of endometrial cancer depending on operative methods. A group of patients who underwent radical hysterectomy and a group of patients who underwent total hysterectomy were compared with each other in the overall survival. (a) Comparison in all patients groups. (b) Comparison in the RFP negative group. (c) Comparison in the RFP positive group.
Figure 11:
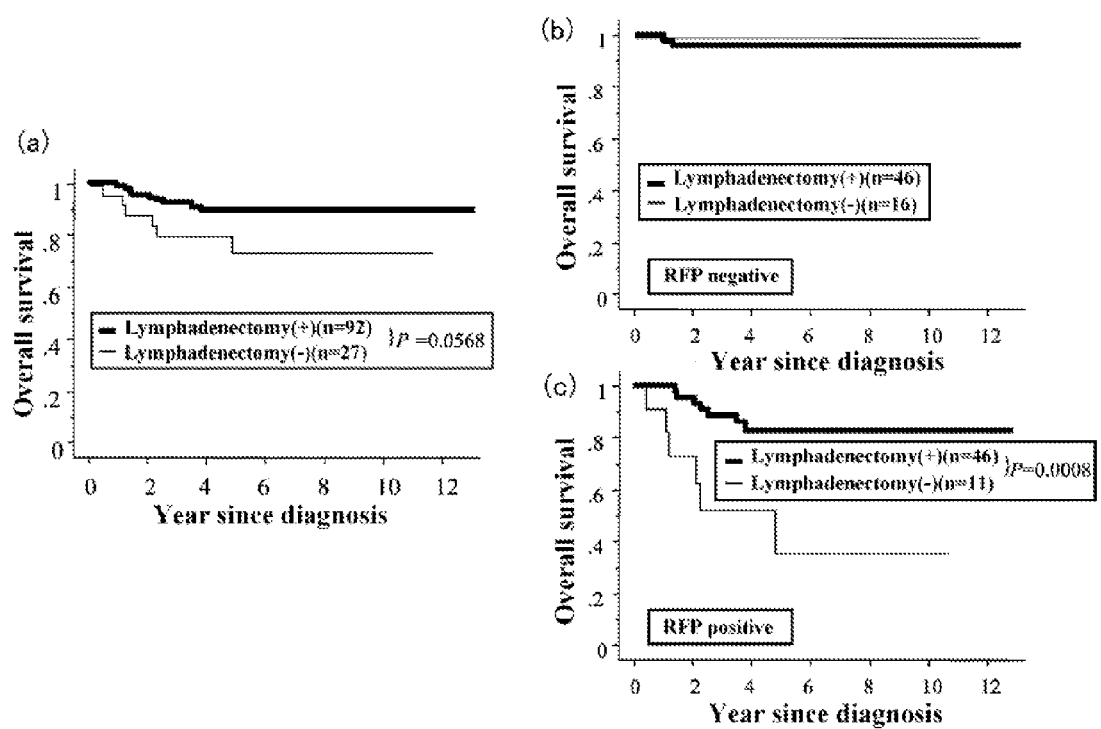
[FIG. 11] Graphs showing the RFP expression and the difference of prognoses of endometrial cancer depending on operative methods. A group of patients who underwent lymphadenectomy and a group of patients who did not undergo lymphadenectomy were compared with each other in the overall survival. (a) Comparison in all patients groups. (b) Comparison in the RFP negative group. (c) Comparison in the RFP positive group.

For further investigation, the relation between the expression of RFP in endometrial cancer and prognosis was examined. As a result, in the investigation of all patients groups (FIG. 9(a)), it was shown that prognosis was significantly poor in a patients group in which the expression of RFP was observed. Furthermore, when the same investigation was carried out by dividing patients groups into stage I and stages II to IV, the expression of RFP correlates to poor prognosis regardless of stages (FIG. 9(b)(c)). Subsequently, the relation between the expression of RFP and the prognosis was compared between patients groups in which different operations were employed respectively. Herein, the difference between radical hysterectomy and total hysterectomy was investigated. As a result, in the RFP negative group, no significant difference in prognosis based on the difference in operative method is not observed (FIG. 10(b)), but in the RFP positive group, the prognosis is significantly improved in the radical hysterectomy group as compared with the total hysterectomy group (FIG. 10(c)). On the other hand, the difference based on the presence or absence of lymphadenectomy was investigated. In the RFP negative group, no significant difference between both groups (a patients group (+) that underwent lymphadenectomy and a patients group (−) that did not undergo lymphadenectomy) (FIG. 11(b)). However, in the RFP positive group, it was shown that prognosis was improved in a group that underwent lymphadenectomy as compared with a patient group that did not undergo lymphadenectomy (FIG. 11(c)). With the consideration of the results of both FIGS. 10 and 11 together, for patients in which expression of RFP is observed, it can be thought that employing more aggressive operation leads to improvement of prognosis. It can be said that information for selecting a operative method can be obtained by confirming the state of expression of RFP (for example, immunostaining is carried out) in biopsy for diagnosis of endometrial cancer.

[Industrial Applicability]

An action enhancing agent of the present invention brings a method of cancer treatment with less adverse effect. The action enhancing agent of the present invention is used in combination with treatment using an anticancer drug having the oxidative stress-inducing ability. Also when two or more types of anticancer drugs are used in combination, the action enhancing agent of the present invention can be applied.

The present invention is not limited to the description of the above embodiments and Examples. A variety of modifications, which are within the scopes of the following claims and which are easily achieved by a person skilled in the art, are included in the present invention.

Contents of the theses, Publication of Patent Applications, Patent Publications, and other published documents referred to in this specification are herein incorporated by reference in its entity.

REFERENCES

1. Yang, X J. and Seto, E. The Rpd3/Hda1 family of lysine deacetylases: from bacteria and yeast to mice and men. Nat Rev Mol Cell Biol. 9(3):206-18 (2008)
2. Bolden, J E., Peart, M J. and Johnstone, R W. Anticancer activities of histone deacetylase inhibitors. Nat Rev Drug Discov. 5(9):769-84 (2006).
3. Minucci, S. and Pelicci, P G Histone deacetylase inhibitors and the promise of epigenetic (and more) treatments for cancer. Nature Reviews Cancer. 6(1):38-51 (2006).
4. Junn, E. et al. Vitamin D3 up-regulated protein 1 mediates oxidative stress via suppressing the thioredoxin function. J Immunol. 164(12):6287-95 (2000).
5. Xu, W S., Parmigiani, R B. and Marks, P A. Histone deacetylase inhibitors: molecular mechanisms of action. Oncogene. 26(37):5541-52 (2007).
6. Marks, P A. and Breslow, R. Dimethyl sulfoxide to vorinostat: development of this histone deacetylase inhibitor as an anticancer drug. Nature Biotechnology. 25(1):84-90 (2007).
7. Miyajima, A. et al. Role of reactive oxygen species in cis-dichlorodiammineplatinum-induced cytotoxicity on bladder cancer cells. Br J Cancer. 76(2):206-10 (1997).
8. Kurosu, T., Fukuda, T., Miki, T. and Miura, O. BCL6 overexpression prevents increase in reactive oxygen species and inhibits apoptosis induced by chemotherapeutic reagents in B-cell lymphoma cells. Oncogene. 22(29):4459-68 (2003).
9. Hwang, I T. et al. Drug resistance to 5-FU linked to reactive oxygen species modulator 1. Biochem Biophys Res Commun. 359(2):304-10 (2007).
10. Ravid, A. et al. 1,25-Dihydroxyvitamin D3 enhances the susceptibility of breast cancer cells to doxorubicin-induced oxidative damage. Cancer Res. 59(4):862-7 (1999).
11. Godwin, A K. et al. High resistance to cisplatin in human ovarian cancer cell lines is associated with marked increase of glutathione synthesis. Proc Natl Acad Sci USA. 89(7):3070-4 (1992).
12. Yokomizo, A. et al. Cellular levels of thioredoxin associated with drug sensitivity to cisplatin, mitomycin C, doxorubicin and etoposide. Cancer Res. 55(19):4293-6 (1995).
13. Sasada, T. et al. Redox control of resistance to cis-diamminedichloroplatinum (II) (CDDP): protective effect of human thioredoxin against CDDP-induced cytotoxicity. J Clin Invest. 97(10):2268-76 (1996).
14. Powis, G and Kirkpatrick, D L. Thioredoxin signaling as a target for cancer therapy. Curr Opin Pharmacol. 7(4):392-7 (2007).
15. Butler, L M. et al. The histone deacetylase inhibitor SAHA arrests cancer cell growth, up-regulates thioredoxin-binding protein-2, and down-regulates thioredoxin. Proc Natl Acad Sci USA. 99(18):11700-5 (2002).
16. Luo, J. Deacetylation of p53 modulates its effect on cell growth and apoptosis. Nature. 408(6810):377-81 (2000).
17. Ito, A. et al. MDM2-HDAC1-mediated deacetylation of p53 is required for its degradation. EMBO J. 21(22):6236-45 (2002).
18. Insinga, A. et al Impairment of p53 acetylation, stability and function by an oncogenic transcription factor. EMBO J. 23(5):1144-54 (2004).
19. Shimono, Y. et al. Mi-2 beta associates with BRG1 and RET finger protein at the distinct regions with transcriptional activating and repressing abilities. J Biol Chem. 278(51):51638-45 (2003).
20. Shimono, Y. et al. RET finger protein is a transcriptional repressor and interacts with enhancer of polycomb that has dual transcriptional functions. J Biol Chem. 275(50):39411-9 (2000).
21. Nishiyama, A. et al. Identification of thioredoxin-binding protein-2/vitamin D(3) up-regulated protein 1 as a negative regulator of thioredoxin function and expression. J Biol Chem. 274(31):21645-50 (1999).
22. Wang, Y., De Keulenaer, G W. and Lee, R T. Vitamin D(3)-up-regulated protein-1 is a stress-responsive gene that regulates cardiomyocyte viability through interaction with thioredoxin. J Biol Chem. 277(29):26496-500 (2002).
23. Baker, A F. et al. Identification of thioredoxin-interacting protein 1 as a hypoxia-inducible 1alpha-induced gene in pancreatic cancer. Pancreas. 36(2):178-86. (2008).
24. Cao, T., Borden, K L., Freemont, P S. and Etkin, L D. Involvement of the rfp tripartite motif in protein-protein interactions and subcellular distribution. J Cell Sci. 110 (Pt 14):1563-71 (1997).
25. Li, X. et al. Unique features of TRIM5alpha among closely related human TRIM family members. Virology. 360(2):419-33 (2007).
26. Kelly, W K., O'Connor, O A. and Marks, P A. Histone deacetylase inhibitors: from target to clinical trials. Expert Opin Investig Drugs. 11(12):1695-713 (2002).
27. Tezel, G et al. M. Different nuclear/cytoplasmic distributions of RET finger protein in different cell types. Pathol Int. 49(10):881-6 (1999)
28. Shimono, K. et al. Microspherule protein 1, Mi-2beta, and RET finger protein associate in the nucleolus and up-regulate ribosomal gene transcription. J Biol Chem. 280(47):39436-47 (2005)

The invention claimed is:

1. A method for estimating prognosis in a cancer patient having endometrial cancer comprising:

determining an amount of RFP (RET finger protein) in a cancer cell from the patient, and comparing the amount of RFP with a reference amount of RFP wherein an increase in RFP relative to the reference amount is indicative of poor prognosis.

2. The method of claim 1, wherein an increase in RFP relative to the reference amount is indicative of poor prognosis regardless of cancer stage.

3. The method of claim 1, further comprising the step of managing patient treatment.

4. The method of claim 3, wherein managing patient treatment is performing lymphadenectomy if the amount of RFP is increased relative to the reference amount.

* * * * *